US006034072A

United States Patent [19]
Ralston et al.

[11] Patent Number: 6,034,072
[45] Date of Patent: Mar. 7, 2000

[54] IL-2 GENE EXPRESSION AND DELIVERY SYSTEMS AND USES

[75] Inventors: Robert Ralston; Susanne Muller; Russ Mumper, all of The Woodlands, Tex.; William Munger, Bethesda, Md.; Maria Bruno, The Woodlands, Tex.

[73] Assignee: Genemedicine, Inc., The Woodlands, Tex.

[21] Appl. No.: 09/012,366

[22] Filed: Jan. 23, 1998

Related U.S. Application Data

[60] Provisional application No. 60/039,709, Feb. 10, 1997.

[51] Int. Cl.$^7$ ............................. A61K 48/00; C12N 15/63
[52] U.S. Cl. ........................................... 514/44; 435/320.1
[58] Field of Search .............................. 514/44; 424/417, 424/420; 435/172.3, 6, 69.1, 320.1

[56] References Cited

U.S. PATENT DOCUMENTS

| | | | |
|---|---|---|---|
| 4,738,927 | 4/1988 | Taniguchi et al. | 435/243 |
| 4,897,355 | 1/1990 | Eppstein et al. | 435/240.2 |
| 5,703,055 | 12/1997 | Felgner et al. | 514/44 |
| 5,827,703 | 10/1998 | Debs et al. | 435/172.3 |

FOREIGN PATENT DOCUMENTS

| | | |
|---|---|---|
| 90/11092 | 10/1990 | WIPO . |
| 93/12756 | 7/1993 | WIPO . |
| 93/18759 | 9/1993 | WIPO . |
| 93/19768 | 10/1993 | WIPO . |
| 93/24640 | 12/1993 | WIPO . |
| 96/17063 | 6/1996 | WIPO . |

OTHER PUBLICATIONS

Anderson, Ed., "Recombinant DNA Advisory Committee (RAC) Data Management Report," Dec., *Human Gene Therapy* 6:535–548 (1994).
Brinster et al., "Introns Increase Transcriptional Efficiency in Transgenic Mice," *Proc. Natl. Acad. Sci. USA*, 85:836–840 (1988).
Chen et al., "Bipartite Structure of the Downstream Element of the Mouse Beta Globin (major) Poly(A) Signal," *Nucl. Acids Res.* 20:2565–2572 (1992).
Choi et al., "A Generic Intron Increases Gene Expression in Transgenic Mice" *Mol. Cell Biol.* 11:3070–3074 (1991).
Evans et al., "Introns in the 3'–untranslated Region can Inhibit Chimeric CAT and β–galactosidase Gene Expression," *Gene* 84:135–142 (1989).
Fitzwater et al., "Conditional High Copy No. ColE1 Mutants: Resistance to RNA1 Inhibition in vivo and in vitro," *EMBO J* 7:3289–3297 (1988).
Gao et al., "Cationic Liposome–mediated Gene Transfer," *Gene Therapy* 2:710–722 (1995).
Ghersa et al., "Commonly Used cat Reporter Vectors Contain a cAMP–Inducible, Crpytic Enhancer that Co–operates with NF–KB–sites," *Gene* 151:331–332 (1994).
Gil et al., "A Sequence Downstream of AAUAAA is Required for Rabbit β–globin mRNA 3'–End Formation," *Nature* 312:473–474 (1984).
Gil et al., Position–dependent Sequence Elements Downstream of AAUAAA are Required for Efficient Rabbit β–Globin mRNA 3' End Formation *Cell* 49:399–406 (1987).
Hawkins, "A Survey on Intron and Exon Legths," *Nucl. Acids Res.* 16:9893–9909 (1988).
Hofland et al., "Inhibtion of Human Ovarian Carcinoma Cell Proliferation by Liposome–Plasmid DNA Complex," *Biochem. Biophys. Res. Comm.* 207:492–496 (1995).
Huang et al., "The Simian Virus 40 Small–t Intron, Present in Many Common Expression Vectors, Leads to Aberrant Splicing," *Mol. Cell Biol.* 10:1805–1810 (1990).
Jackson et al., "Do the Poly(A) Tail and 3' Untranslated Region Control mRNA Translation?," *Cell* 62:15–24 (1990).
Kozak, "Determinants of Translational Fidelty and Efficiency in Vertebrate mRNAs," *Biochemie* 76:815–821 (1994).
Kushner et al., "Eukaryotic Regulatory Elements Lurking in Plasmid DNA: The Activator Protein–1 Site in pUC," *Molecular Endocrinology.* 8:405–407 (1994).
Leite et al., "Negative Effect of a cis–acting pBR322 Element on Adenovirus E1a Gene Expression," *Gene* 82:351–356 (1989).
Lusky et al., "Inhbition of SV40 Replication in Simian Cells by Specific pBR322 DNA Sequences," *Nature* 293:79–81 (1981).
Palmiter et al., "Heterologous Introns can Enhance Expression of Transgenes in Mice," *Proc. Natl. Acad. Sci. USA* 88:478–482 (1991).
Parker et al., "Plasmid DNA Gene Therapy: Studies with the Human Interleukin–2 Gene in Tumor Cells in vitro and in the Murine B16 Melanoma Model in vivo," *Cancer Gene Ther.* 3:175–185 (1996).
Peterson et al., "Context–Dependent Gene Expression: cis–Acting Negative Effects of Specific Procaryotic Plasmid Sequences on Eucaryotic Genes," *Molecular and Cellular Biology* 7:1563–1567 (1987).
Proudfoot, "Poly(A) Signals," *Cell* 64:671–674 (1991).
Sato et al., "Immunostimulatory DNA Sequences Necessary for Effective Intradermal Gene Immunization," *Science* 273:352–354 (1996).
Smith, "Regulatory Considerations for Nucleic Acid Vaccines," *Vaccine* 12(16):1515–1519 (1994).
Suzuki et al., *An Introduction to Genetic Analysis*, p. 404 (1989).
Szala et al., "The Use of Cationic Liposomes DC–CHOL/DOPE and DDAB/DOPE for Direct Transfer of Escherichia coli Cytosine Deaminase Gene into Growing Melanoma Tumors," *Gene Therapy* 3:1026–1031 (1996).

(List continued on next page.)

*Primary Examiner*—Bruce R. Campell
*Assistant Examiner*—Anne Marie S. Beckerleg
*Attorney, Agent, or Firm*—Lyon & Lyon LLP

[57] ABSTRACT

Plasmid expression systems for delivery of DNA coding sequences to a mammal are described which provide expression of human IL-2. Also described are particular lipid/DNA delivery systems having advantageous characteristics of size, charge ratio, and proportion of supercoiled DNA, and methods of preparing and using such delivery systems for treatment.

17 Claims, 14 Drawing Sheets

OTHER PUBLICATIONS

Tully et al., "pBR322 Contains Glucocorticoid Regulatory Element DNA Consensus Sequences," *Biochemical and Biophysical Research Communications* 144:1–10 (1987).

Uhlin et al., "A Runaway–replication Mutant of Plasmid R1drd–19: Temperature–Dependent Loss of Copy Number Control," *Mol. Gen. Genet.* 165:167–179 (1978).

Ulfendahl et al., "Splicing of the Adenovirus–2 EIA 13S mRNA Requires a Minimal Intron Length and Specific Intron Signals," *Nucl. Acids Res.* 13:6299–6315 (1985).

Yamamoto et al., "Lipofection of Synthetic Oligodeoxyribonucleotide having a Palindromic Sequence of AACGTT to Murine Splenocytes Enhances Interferon Production and Natural Killer Activity," *Microbiol. Immunol.* 38(10):831–836 (1994).

Yoder et al., "Procaryotic Genomic DNA Inhibits Mammalian Cell Transformation," *Molecular and Cellular Biology* 3:956–959 (1983).

Demolder et al. (1992) Gene, vol. 111, 207–213.

Funk et al. (1990) Biochemistry, vol. 29, 1654–1660.

Mumper et al. (1996) Pharmaceutical Research, vol. 13 (5), 701–709.

Ross et al. (1996) Human Gene Therapy, vol. 7, 1781–1790.

Verma et al. (1997) Nature, vol. 389, 239–242.

Orkin et al. (1995) "Report and Recommendations of the Panel to Assess the NIH Investment in Gene therapy".

| AmAcid | Codon | Number | /1000 | Fraction |
|---|---|---|---|---|
| Gly | GGG | 905.00 | 18.76 | 0.24 |
| Gly | GGA | 525.00 | 10.88 | 0.14 |
| Gly | GGT | 441.00 | 9.14 | 0.12 |
| Gly | GGC | 1867.00 | 38.70 | 0.50 |
| Glu | GAG | 2420.00 | 50.16 | 0.75 |
| Glu | GAA | 792.00 | 16.42 | 0.25 |
| Asp | GAT | 592.00 | 12.27 | 0.25 |
| Asp | GAC | 1821.00 | 37.75 | 0.75 |
| Val | GTG | 1866.00 | 38.68 | 0.64 |
| Val | GTA | 134.00 | 2.78 | 0.05 |
| Val | GTT | 198.00 | 4.10 | 0.01 |
| Val | GTC | 728.00 | 15.09 | 0.25 |
| Ala | GCG | 652.00 | 13.51 | 0.17 |
| Ala | GCA | 488.00 | 10.12 | 0.13 |
| Ala | GCT | 654.00 | 13.56 | 0.17 |
| Ala | GCC | 2057.00 | 42.64 | 0.53 |
| Arg | AGG | 512.00 | 10.61 | 0.18 |
| Arg | AGA | 298.00 | 6.18 | 0.10 |
| Ser | AGT | 354.00 | 7.34 | 0.10 |
| Ser | AGC | 1171.00 | 24.27 | 0.34 |
| Lys | AAG | 2117.00 | 43.88 | 0.82 |
| Lys | AAA | 471.00 | 9.76 | 0.18 |
| Asn | AAT | 314.00 | 6.51 | 0.22 |
| Asn | AAC | 1120.00 | 23.22 | 0.78 |
| Met | ATG | 1077.00 | 22.32 | 1.00 |
| Ile | ATA | 88.00 | 1.82 | 0.05 |
| Ile | ATT | 315.00 | 6.53 | 0.18 |
| Ile | ATC | 1369.00 | 28.38 | 0.17 |
| Thr | ACG | 405.00 | 8.40 | 0.15 |
| Thr | ACA | 373.00 | 7.73 | 0.14 |
| Thr | ACT | 358.00 | 7.42 | 0.14 |
| Thr | ACC | 1502.00 | 31.13 | 0.57 |
| Trp | TGG | 652.00 | 13.51 | 1.00 |
| End | TGA | 109.00 | 2.26 | 0.55 |
| Cys | TGT | 325.00 | 6.74 | 0.32 |
| Cys | TGC | 706.00 | 14.63 | 0.68 |
| End | TAG | 42.00 | 0.87 | 0.21 |
| End | TAA | 46.00 | 0.95 | 0.23 |
| Tyr | TAT | 360.00 | 7.46 | 0.26 |
| Tyr | TAC | 1042.00 | 21.60 | 0.74 |
| Leu | TTG | 313.00 | 6.49 | 0.06 |
| Leu | TTA | 76.00 | 1.58 | 0.02 |
| Phe | TTT | 336.00 | 6.96 | 0.20 |
| Phe | TTC | 1377.00 | 28.54 | 0.80 |
| Ser | TCG | 325.00 | 6.74 | 0.09 |
| Ser | TCA | 165.00 | 3.42 | 0.05 |
| Ser | TCT | 450.00 | 9.33 | 0.13 |
| Ser | TCC | 958.00 | 19.86 | 0.28 |
| Arg | CGG | 611.00 | 12.67 | 0.21 |
| Arg | CGA | 183.00 | 3.79 | 0.06 |
| Arg | CGT | 210.00 | 4.35 | 0.07 |
| Arg | CGC | 1086.00 | 22.51 | 0.37 |
| Gln | CAG | 2020.00 | 41.87 | 0.88 |

*Fig. 5A*

| AmAcid | Codon | Number | /1000 | Fraction |
|--------|-------|--------|-------|----------|
| Gln | CAA | 283.00 | 5.87 | 0.12 |
| His | CAT | 234.00 | 4.85 | 0.21 |
| His | CAC | 870.00 | 18.03 | 0.79 |
| Leu | CTG | 2884.00 | 59.78 | 0.58 |
| Leu | CTA | 166.00 | 3.44 | 0.03 |
| Leu | CTT | 238.00 | 4.93 | 0.05 |
| Leu | CTC | 1276.00 | 26.45 | 0.26 |
| Pro | CCG | 482.00 | 9 99 | 0.17 |
| Pro | CCA | 456.00 | 9.45 | 0.16 |
| Pro | CCT | 568.00 | 11.77 | 0.19 |
| Pro | CCC | 1410.00 | 29.23 | 0.48 |

β-alanyl CHOLESTEROL

DC-chol

SEQUENCE LISTING (1) GENERAL INFORMATION:

(iii) NUMBER OF SEQUENCES:      11

(2) INFORMATION FOR SEQ ID NO: 1:

(i) SEQUENCE CHARACTERISTICS:
        (A) LENGTH:        462 base pairs
        (B) TYPE:          nucleic acid
        (C) STRANDEDNESS:  single
        (D) TOPOLOGY:      linear (xi) SEQUENCE DESCRIPTION: SEQ ID NO: 1:

```
ATGTACAGGA TGCAACTCCT GTCTTGCATT GCACTAAGTC TTGCACTTGT CACAAACAGT      60

GCACCTACTT CAAGTTCTAC AAAGAAAACA CAGCTACAAC TGGAGCATTT ACTGCTGGAT     120

TTACAGATGA TTTTGAATGG AATTAATAAT TACAAGAATC CCAAACTCAC CAGGATGCTC     180

ACATTTAAGT TTTACATGCC CAAGAAGGCC ACAGAACTGA AACATCTTCA GTGTCTAGAA     240

GAAGAACTCA AACCTCTGGA GGAAGTGCTA AATTTAGCTC AAAGCAAAAA CTTTCACTTA     300

AGACCCAGGG ACTTAATCAG CAATATCAAC GTAATAGTTC TGGAACTAAA GGGATCTGAA     360

ACAACATTCA TGTGTGAATA TGCTGATGAG ACAGCAACCA TTGTAGAATT TCTGAACAGA     420

TGGATTACCT TTTGTCAAAG CATCATCTCA ACACTGACTT GA                        462
```

(2) INFORMATION FOR SEQ ID NO: 2:

(i) SEQUENCE CHARACTERISTICS:
        (A) LENGTH:        462 base pairs
        (B) TYPE:          nucleic acid

```
            (C) STRANDEDNESS:     single
            (D) TOPOLOGY:         linear (xi) SEQUENCE DESCRIPTION: SEQ ID NO: 2:

ATGTACCGCA TGCAGCTGCT GAGCTGCATC GCCCTGAGCC TGGCCCTGGT GACCAACAGC    60

GCCCCCACCA GCAGCAGCAC CAAGAAGACC CAGCTGCAGC TGGAGCACCT GCTGCTGGAC   120

CTGCAGATGA TCCTGAACGG CATCAACAAC TACAAGAACC CCAAGCTGAC CCGCATGCTG   180

ACCTTCAAGT TCTACATGCC CAAGAAGGCC ACCGAGCTGA AGCACCTGCA GTGCCTGGAG   240

GAGGAGCTGA AGCCCCTGGA GGAGGTGCTG AACCTGGCCC AGAGCAAGAA CTTCCACCTG   300

CGCCCCCGCG ACCTGATCAG CAACATCAAC GTGATCGTGC TGGAGCTGAA GGGCAGCGAG   360

ACCACCTTCA TGTGCGAGTA CGCCGACGAG ACCGCCACCA TCGTGGAGTT CCTGAACCGC   420

TGGATCACCT TCTGCCAGAG CATCATCAGC ACCCTGACCT GA                      462

(2) INFORMATION FOR SEQ ID NO: 3:

(i) SEQUENCE CHARACTERISTICS:
            (A) LENGTH:          153 amino acids
            (B) TYPE:            amino acid
            (C) STRANDEDNESS:    single
            (D) TOPOLOGY:        linear (ii) MOLECULE TYPE:       Peptide (xi) SEQUENCE DESCRIPTION: SEQ ID NO: 3:
```

Met Tyr Arg Met Gln Leu Leu Ser Cys Ile Ala Leu Ser Leu Ala Leu
 1               5                  10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
 50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

```
(2) INFORMATION FOR SEQ ID NO: 4:

(i) SEQUENCE CHARACTERISTICS:
            (A) LENGTH:          191 base pairs
            (B) TYPE:            nucleic acid
            (C) STRANDEDNESS:    single
            (D) TOPOLOGY:        linear (xi) SEQUENCE DESCRIPTION: SEQ ID NO: 4:

GGGTGGCATC CCTGTGACCC CTCCCCAGTG CCTCTCCTGG CCCTGGAAGT TGCCACTCCA    60

GTGCCCACCA GCCTTGTCCT AATAAAATTA AGTTGCATCA TTTTGTCTGA CTAGGTGTCC   120
```

-continued

```
TTCTATAATA TTATGGGGTG GAGGGGGGTG GTATGGAGCA AGGGGCAAGT TGGGAAGACA    180

ACCTGTAGGG C                                                        191
```

(2) INFORMATION FOR SEQ ID NO: 5:

(i) SEQUENCE CHARACTERISTICS:
        (A) LENGTH:       58 base pairs
        (B) TYPE:         nucleic acid
        (C) STRANDEDNESS:  single
        (D) TOPOLOGY:     linear (xi) SEQUENCE DESCRIPTION: SEQ ID NO: 5:

```
AAGCTTACTC AACACAATAA CAAACTTACT TACAATCTTA ATTAACAGGC CACCATGG      58
```

(2) INFORMATION FOR SEQ ID NO: 6:

(i) SEQUENCE CHARACTERISTICS:
        (A) LENGTH:       15 base pairs
        (B) TYPE:         nucleic acid
        (C) STRANDEDNESS:  single
        (D) TOPOLOGY:     linear (xi) SEQUENCE DESCRIPTION: SEQ ID NO: 6:

```
CAGGTAAGTG TCTTC                                                    15
```

(2) INFORMATION FOR SEQ ID NO: 7:

(i) SEQUENCE CHARACTERISTICS:
        (A) LENGTH:       30 base pairs
        (B) TYPE:         nucleic acid
        (C) STRANDEDNESS:  single
        (D) TOPOLOGY:     linear (xi) SEQUENCE DESCRIPTION: SEQ ID NO: 7:

```
TACTAACGGT TCTTTTTTTC TCTTCACAGG                                     30
```

(2) INFORMATION FOR SEQ ID NO: 8:

(i) SEQUENCE CHARACTERISTICS:
        (A) LENGTH:       271 base pairs
        (B) TYPE:         nucleic acid
        (C) STRANDEDNESS:  single
        (D) TOPOLOGY:     linear (xi) SEQUENCE DESCRIPTION: SEQ ID NO: 8:

```
TCTAGAGCAT TTTTCCCTCT GCCAAAAATT ATGGGACAT CATGAAGCCC CTTGAGCATC    60

TGACGTCTGG CTAATAAAGG AAATTTATTT TCATTGCAAT AGTGTGTTGG AATTTTTTGT   120

GTCTCTCACT CGGTACTAGA GCATTTTTCC CTCTGCCAAA AATTATGGGG ACATCATGAA   180

GCCCCTTGAG CATCTGACGT CTGGCTAATA AAGGAAATTT ATTTTCATTG CAATAGTGTG   240

TTGGAATTTT TTGTGTCTCT CACTCGGTAC C                                  271
```

(2) INFORMATION FOR SEQ ID NO: 9:

(i) SEQUENCE CHARACTERISTICS:
        (A) LENGTH:       34 base pairs
        (B) TYPE:         nucleic acid
        (C) STRANDEDNESS:  single
        (D) TOPOLOGY:     linear (ix) FEATURE:
        (D) OTHER INFORMATION:   "N" stands for any base.

(xi) SEQUENCE DESCRIPTION: SEQ ID NO: 9:

```
ATGCGTCACG ACGAGATCCT CGCCGTCGGN CATG                               34
```

(2) INFORMATION FOR SEQ ID NO: 10:

(i) SEQUENCE CHARACTERISTICS:
        (A) LENGTH:        26 base pairs
        (B) TYPE:          nucleic acid
        (C) STRANDEDNESS:  single
        (D) TOPOLOGY:      linear (xi) SEQUENCE DESCRIPTION: SEQ ID NO: 10:

GCAGTGCTGC TCTAGGAGCG GCAGCC                             26

(2) INFORMATION FOR SEQ ID NO: 11:

(i) SEQUENCE CHARACTERISTICS:
        (A) LENGTH:        16 base pairs
        (B) TYPE:          nucleic acid
        (C) STRANDEDNESS:  single
        (D) TOPOLOGY:      linear (ix) FEATURE:
        (D) OTHER INFORMATION:  "Y" stands for C or T.
            "N" stands for any base.

(xi) SEQUENCE DESCRIPTION: SEQ ID NO: 11:

YYYYYYYYYY YNYAGG                                            16

IL-2 GENE EXPRESSION AND DELIVERY SYSTEMS AND USES

CROSS-REFERENCE TO RELATED APPLICATIONS

This application claims the benefit of Ralston et al., U.S. Provisional Application 60/039,709, entitled "IL-2 GENE EXPRESSION AND DELIVERY SYSTEMS USES", filed Feb. 10, 1997. This application is hereby incorporated herein by reference in its entirety, including any drawings and figures.

BACKGROUND OF THE INVENTION

The following discussion of the background and of the invention is merely provided to aid the reader in understanding the invention and is not admitted to describe or constitute prior art to the present invention.

The present invention relates to gene delivery and gene therapy, and provides novel nucleic acid constructs for expression of human IL-2 in a mammal, formulations for delivery that incorporate a nucleic acid construct for expression, and methods for preparing and using such constructs and formulations. In particular, this invention relates to plasmid constructs for delivery of therapeutic IL-2 encoding nucleic acids to cells and to modulation of cytokine activity. In addition, this invention relates to methods of using those constructs as well as methods for preparing such constructs.

Plasmids are an essential element in genetic engineering and gene therapy. Plasmids are circular DNA molecules that can be introduced into bacterial cells by transformation which replicate autonomously in the cell. Plasmids allow for the amplification of cloned DNA. Some plasmids are present in 20 to 50 copies during cell growth, and after the arrest of protein synthesis, as many as 1000 copies per cell of a plasmid can be generated. (Suzuki et al., *Genetic Analysis*, p. 404, (1989).)

Current non-viral approaches to human gene therapy require that a potential therapeutic gene be cloned into plasmids. Large quantities of a bacterial host harboring the plasmid may be fermented and the plasmid DNA may be purified for subsequent use. Current human clinical trials using plasmids utilize this approach. (Recombinant DNA Advisory Committee Data Management Report, December, 1994, *Human Gene Therapy* 6: 535–548). Studies normally focus on the therapeutic gene and the elements that control its expression in the patient when designing and constructing gene therapy plasmids. Generally, therapeutic genes and regulatory elements are simply inserted into existing cloning vectors that are convenient and readily available.

Plasmid design and construction utilizes several key factors. First, plasmid replication origins determine plasmid copy number, which affects production yields. Plasmids that replicate to higher copy number can increase plasmid yield from a given volume of culture, but excessive copy number can be deleterious to the bacteria and lead to undesirable effects (Fitzwater, et al., *Embo J*. 7: 3289–3297 (1988); Uhlin, et al., *Mol. Gen. Genet*. 165: 167–179 (1979)). Artificially constructed plasmids are sometimes unstably maintained, leading to accumulation of plasmid-free cells and reduced production yields.

To overcome this problem of plasmid-free cells, genes that code for antibiotic resistance phenotype are included on the plasmid and antibiotics are added to kill or inhibit plasmid-free cells. Most general purpose cloning vectors contain ampicillin resistance (β-lactamase, or bla) genes. Use of ampicillin can be problematic because of the potential for residual antibiotic in the purified DNA, which can cause an allergic reaction in a treated patient. In addition, β-lactam antibiotics are clinically important for disease treatment. When plasmids containing antibiotic resistance genes are used, the potential exists for the transfer of antibiotic resistance genes to a potential pathogen.

Other studies have used the neo gene which is derived from the bacterial transposon Tn5. The neo gene encodes resistance to kanamycin and neomycin (Smith, *Vaccine* 12: 1515–1519 (1994)). This gene has been used in a number of gene therapy studies, including several human clinical trials (Recombinant DNA Advisory Committee Data Management Report, December, 1994, *Human Gene Therapy* 6: 535–548). Due to the mechanism by which resistance is imparted, residual antibiotic and transmission of the gene to potential pathogens may be less of a problem than for β-lactams.

In addition to elements that affect the behavior of the plasmid within the host bacteria, such as *E. coli*, plasmid vectors have also been shown to affect transfection and expression in eukaryotic cells. Certain plasmid sequences have been shown to reduce expression of eukaryotic genes in eukaryotic cells when carried in cis (Peterson, et al., *Mol. Cell. Biol.* 7: 1563–1567 (1987); Yoder and Ganesan, *Mol. Cell. Biol.* 3: 956–959 (1983); Lusky and Botchan, *Nature* 293: 79–81 (1981); and Leite, et al., *Gene* 82: 351–356 (1989)). Plasmid sequences also have been shown to fortuitously contain binding sites for transcriptional control proteins (Ghersa, et al., *Gene* 151: 331–332 (1994); Tully and Cidlowski, *Biochem. Biophys. Res. Comm.* 144: 1–10 (1987); and Kushner, et al., *Mol. Endocrinol.* 8: 405–407 (1994)). This can cause inappropriate levels of gene expression in treated patients.

Interleukin-2 (IL-2) is, among other functions, involved in stimulating the proliferation of helper T cells, in particular $T_H1$ cells by an autocrine mechanism. Secretion of IL-2 will also stimulate the proliferation of other activated helper T cells and cytotoxic T cells.

Based on these and other responses to IL-2, attempts have been made to use IL-2 in anti-tumor therapy. IL-2 polypeptide can be isolated from stimulated $T_H1$ cells or produced from a recombinant IL-2 gene. Such a recombinant gene is described, for example, in Taniguchi et al., U.S. Pat. No. 4,738,927, along with cells containing the recombinant gene. However, administration of high doses of IL-2 polypeptide results in significant toxicity-related side effects, such as fever, fluid retention, and vascular leak syndrome. In addition, administration of polypeptide must be repeated at short intervals due to a short half-life for the injected polypeptide.

As an example of an alternative, Hobart et al., PCT application PCT/US95/15020, International publication WO 96/17063, describes a plasmid encoding human IL-2, in which a natural human IL-2 coding sequence is part of an expression facilitating sequence which also contains a cytomegalovirus (CMV) immediate-early promoter region and a transcription termination/polyadenylation signal sequence derived from bovine growth hormone. Formulations for delivery of human IL-2 coding sequence are also described which included the IL-2 encoding plasmid with DMRIE/DOPE or βAE/DOPE at a DNA:lipid mass ratio of 5:1.

SUMMARY OF THE INVENTION

The present invention provides compositions and methods for delivery of particular functional IL-2 coding sequences to a mammal. These compositions are prepared and administered in such a manner that the encoded gene products are expressed in the mammal to which the composition is administered. As a result, these compositions and methods are useful in gene therapy since the coding sequence encode a molecule having a therapeutic function. These compositions include expression systems, delivery systems, and certain IL-2 coding sequences.

Delivery systems include particularly advantageous formulations of a cationic lipid, a neutral co-lipid and a DNA molecule. Such formulations can be administered to a mammal, for example by delivery to a lung, such that one or more coding sequences on the DNA is expressed in that mammal.

Thus, in a first aspect, the invention provides a plasmid for expression of human IL-2 coding sequence (hIL-2) which includes an expression cassette, which can also be referred to as a transcription unit. The transcription unit includes a transcriptional control sequence, which is transcriptionally linked with an IL-2 coding sequence, and a 3' untranslated region/poly(A) signal obtained from human growth hormone. It is often advantageous to provide on the plasmid a selectable marker such as an antibiotic resistance gene (e.g., a neomycin resistance gene). It is also often advantageous to provide an intron, which may, for example, be located 5' to the IL-2 coding sequence and 3' to the promoter in the transcriptional control sequence.

When such a plasmid is placed in an environment suitable for gene expression, the transcriptional unit will thus express the encoded gene product. The level of expression of the gene product will depend to a significant extent on the strength of the associated promoter and the presence and activation of an associated enhancer element.

Thus, in a preferred embodiment the transcriptional control sequence includes promoter/enhancer sequences such as cytomegalovirus (CMV) promotor/enhancer sequences. However, those skilled in the art will recognize that a variety of other promoter sequences suitable for expression in eukaryotic cells are known and can similarly be used in the constructs of this invention.

As used herein, the term "plasmid" refers to a construct made up of genetic material (i.e., nucleic acids). It includes genetic elements arranged such that an inserted coding sequence can be transcribed in eukaryotic cells. Also, while the plasmid may include a sequence from a viral nucleic acid, such viral sequence does not cause the incorporation of the plasmid into a viral particle, and the plasmid is therefore a non-viral vector. Preferably a plasmid is a closed circular DNA molecule.

The term "expression" refers to the biological production of a product encoded by a coding sequence. In most cases a DNA sequence, including the coding sequence, is transcribed to form a messenger-RNA (mRNA). The messenger-RNA is translated to form a polypeptide product which has a relevant biological activity. However in some cases, an RNA product may have the relevant activity and would thus be regarded as a gene product. Also, the process of expression may involve further processing steps to the RNA product of transcription, such as splicing to remove introns, and/or post-translational processing of a polypeptide product.

The term "transcription unit" or "expression cassette" refers to a nucleotide sequence which contains at least one coding sequence along with sequence elements which direct the initiation and termination of transcription. A transcription unit may however include additional sequences, which may include sequences involved in post-transcriptional or post-translational processes.

The term "coding region" or "coding sequence" refers to a nucleic acid sequence which encodes a particular gene product for which expression is desired, according to the normal base pairing and codon usage relationships. Thus, the coding sequence must be placed in such relationship to transcriptional control elements and to translational initiation and termination codons that a proper length transcript will be produced and will result in translation in the appropriate reading frame to produce a functional desired product.

The term "transcriptional control sequence" refers to sequences which control the rate of transcription of a transcriptionally linked coding region. Thus, the term can include elements such as promoters, operators, and enhancers. For a particular transcription unit, the transcriptional control sequences will include at least a promoter sequence.

In this context, "transcriptionally linked" means that in a system suitable for transcription, transcription will initiate under the direction of the control sequence(s) and proceed through sequences which are transcriptionally linked with that control sequence(s). Preferably no mutation is created in the resulting transcript, which would alter the resulting translation product.

A "5' untranslated region" or "5' UTR" refers to a sequence located 3' to promotor region and 5' of the downstream coding region. Thus, such a sequence, while transcribed, is upstream of the translation initiation codon and therefore is not translated into a portion of the polypeptide product.

A "3' untranslated region/poly(A() signal" or "3' UTR/poly(A) signal" is a sequence located downstream (i.e., 3') of the region encoding material polypeptide. As with the 5' UTR this region is generally transcribed but not translated. For expression in eukaryotic cells it is generally preferable to include sequence which signals the addition of a poly-A tail. As with other synthetic genetic elements a synthetic 3' UTR/poly(A) signal has a sequence which differs from naturally-occurring UTR elements.

The term "3' untranslated region/poly(A) signal obtained from human growth hormone" refers to a sequence which contains at least part of the sequence of the natural 3' UTR/poly(a) signal from the human growth hormone gene. However, the sequence may be modified, for example by the deletion of ALU repeat sequences. Deletion of such ALU repeat sequences acts to reduce the possibility of homologous recombination between the expression cassette and genomic material in a transfected cell.

"Cytomegalovirus promotor/enhancer sequences" refers to sequences from a cytomegalovirus which are functional in eukaryotic cells as a transcriptional promoter and an upstream enhancer sequence. The enhancer sequence allows transcription to occur at a higher frequency from the associated promoter.

For the plasmids described herein, one or more of a promoter, 5' untranslated region (5' UTR), the 3' UTR/poly (A) signal, and introns may be a synthetic sequence. In this context the term "synthetic" means that the sequence is not provided directly by the sequence of a naturally occurring genetic element of that type but rather is an artificially created sequence (i.e., created by a person by molecular biological methods). While one or more portions of such a synthetic sequence may be the same as portions of naturally occurring sequences, the full sequence over the specified genetic element is different from a naturally occurring genetic element of that type. The use of such synthetic genetic elements allows the functional characteristics of that element to be appropriately designed for the desired function.

Thus, a "synthetic intron" refers to a sequence which is not a naturally occurring intron sequence but which will be removed from an RNA transcript during normal post transcriptional processing. Such introns can be designed to have a variety of different characteristics, in particular such introns can be designed to have a desired strength of splice site.

A "therapeutic molecule" is one which has a pharmacologic activity when administered appropriately to a mammal suffering from a disease or condition. Such a pharmacologic property is one which is expected to be related to a beneficial effect on the course or a symptom of the disease or condition.

A particular example of coding regions suitable for use in the plasmids of this invention are the natural sequences coding for human IL-2. Thus, in a preferred embodiment coding region has a nucleotide sequence which is the same as SEQ ID NO. 1, which is the natural nucleotide sequence encoding human IL-2. However, it may be preferable to have an IL-2 coding sequence which is a synthetic coding sequence. In a preferred embodiment, the IL-2 coding sequence is a synthetic sequence utilizing optimal codon usage, preferably the sequence shown in SEQ ID NO. 2.

Thus, a "sequence coding for the human IL-2" or "a human IL-2 coding sequence" is a nucleic acid sequence which encodes the amino acid sequence of human IL-2, based on the normal base pairing and translational codon usage relationships. It is preferable that the coding sequence encode the exact, full amino acid sequence of natural human IL-2, but this is not essential. The encoded polypeptide may differ from natural human IL-2, so long as the polypeptide retains IL-2 activity, preferably the polypeptide is at least 50%, 75%, 90%, or 97% as active as natural human IL-2, and more preferably fully as active as natural hIL-2. Thus, the polypeptide encoded by the IL-2 coding sequence may differ from a natural hIL-2 polypeptide by a small amount, preferably less than a 15%, 10%, 5%, or 1% change. Such a change may be of one of more different types, such as deletion, addition, or substitution of one or more amino acids.

For delivery of coding sequences for gene expression, it is generally useful to provide a delivery composition or delivery system which includes one or more other components in addition to the nucleic acid sequences. Such a composition can, for example, aid in maintaining the integrity of the DNA and/or in enhancing cellular uptake of the DNA and/or by acting as an immunogenic enhancer, such as by the non-DNA components having an immunostimulatory effect of their own.

Thus, in another aspect, the invention provides such a composition for delivery of DNA in a mammal. Along with the plasmids as described above, the composition preferably includes a cationic lipid, preferably with a co-lipid (preferably a neutral co-lipid).

Preferably the cationic lipid is DOTMA and the neutral co-lipid is cholesterol (chol). DOTMA is 1,2-di-O-octadecenyl-3-trimethylammonium propane, which is described and discussed in Eppstein et al., U.S. Pat. No, 4,897,355, issued Jan. 30, 1990, which is incorporated herein by reference. However, other lipids and lipid combinations may be used in other embodiments. A variety of such lipids are described in Gao & Huang, 1995, *Gene Therapy* 2: 710–722, which is hereby incorporated by reference.

In addition, other components may be used, along with or instead of the lipid components, such as polyvinylpyrrolidone (PVP). Other examples of compounds suitable for use in delivery formulations include, but are not restricted to those described in co-pending U.S. patent applications, Rolland et al., FORMULATED NUCLEIC ACID COMPOSITIONS AND METHODS OF ADMINISTERING THE SAME FOR GENE THERAPY, application Ser. No. 08/372, 213, filed Feb. 10, 1995, and a continuation-in-part of that application, Rolland et al., FORMULATED NUCLEIC ACID COMPOSITIONS AND METHODS OF ADMINISTERING THE SAME FOR GENE THERAPY, application Ser. No. 08/798,974, filed Feb. 10, 1997, which are hereby incorporated by reference in their entireties. When lipids are used, preferably the lipids are prepared as liposomes and combined with a quantity of DNA having IL-2 coding sequences.

Preferably the liposomes are prepared to have an average diameter of between about 20 and 800 nm, more preferably between about 50 and 400 nm, still more preferably between about 75 and 200 nm, and most preferably about 100 nm. Microfluidization is the preferred method of preparation of the liposomes.

In preferred embodiments, the liposomes are prepared in an aqueous carbohydrate solution which is approximately isotonic with mammalian cells. More preferably, the carbohydrate contains about 10% lactose.

As the form of the DNA affects the expression efficiency, it is preferable that a large fraction of the DNA be in supercoiled form. Thus, in preferred embodiments, at least 80, 90, or 95% of the DNA in the composition is supercoiled.

As the charge ratio of the cationic lipid and the DNA is also a significant factor, in preferred embodiments the DNA and the cationic lipid are present is such amounts that the negative to positive charge ratio is about 1:0.5. While preferable, it is not necessary that the ratio be 1:0.5. Thus, preferably the charge ratio for the compositions is between about 1:0.2 and 1:10, more preferably between about 1:0.3 and 1:3, still more preferably between about 1:0.4 and 1:1.5, but most preferably about 1:0.5.

The term "cationic lipid" refers to a lipid which has a net positive charge at physiological pH, and preferably carries no negative charges at such pH. An example of such a lipid is DOTMA. Similarly, "neutral co-lipid" refers to a lipid which has is usually uncharged at physiological pH. An example of such a lipid is cholesterol.

Thus, "negative to positive charge ratio" for the DNA and cationic lipid refers to the ratio between the net negative charges on the DNA compared to the net positive charges on the cationic lipid.

Recognizing that the non-DNA components of a composition can have significant immunostimulatory effects independent of the presence of specific IL-2 coding sequences, in a related aspect the invention provides a composition for delivery and expression of a human IL-2 coding sequence in a mammal. The composition includes DNA containing a transcription unit having a hIL-2 coding sequence and a combination of DOTMA and cholesterol. The lipids are prepared as liposomes having a diameter of about 100 nm. Preferably the composition includes an aqueous carbohydrate solution which is approximately isotonic with human serum, for example, an about 10% lactose solution. The DNA and DOTMA are present in amounts such that the negative to positive charge ratio is about (1:0.5).

In preferred embodiments, the DNA is a plasmid as described in the first aspect above.

In other aspects, the invention provides a methods for preparing a composition as described in the above aspects. Thus, in one aspect the methods involve preparing a DNA molecule which includes a hIL-2 coding sequence, preparing liposomes having an diameter of about 100 nanometer (nm) which include a cationic lipid and a neutral co-lipid, and combining the liposomes with the DNA in such amounts that the DNA and the cationic lipid are present in a negative to positive charge ratio of about 1:0.5.

In a related aspect, the invention provides a method for preparing a composition for delivery and expression of a human IL-2 coding sequence to a mammal by preparing a DNA molecule (a plasmid) which includes a CMV promoter transcriptionally linked with a human IL-2 coding sequence, and a human growth hormone 3'-untranslated region/poly (A) signal, preparing liposomes containing a cationic lipid and a neutral co-lipid, and combining the liposomes and the plasmid.

As in previous aspects, in preferred embodiments the cationic lipid is DOTMA and the neutral co-lipid is cholesterol, and preferably the liposomes have a diameter of about 100 nm. Also preferably the DNA molecule and the cationic lipid are present in such amounts that the negative to positive charge ratio is about (1:0.5).

The invention also provides methods of treating a mammal utilizing the plasmids and compositions as described above. Thus, in another aspect, the invention provides a method of treating a mammalian condition or disease. The method involves administering to a mammal suffering from a condition or disease a therapeutically effective amount of a composition for delivery of a DNA to a mammal. The composition includes DNA which has coding sequences for IL-2, a cationic lipid, and a neutral co-lipid. The DNA and the cationic lipid are present in such amounts as to result in a negative to positive charge ratio of about 1:0.5. Preferably the cationic lipid and neutral co-lipid are DOTMA and cholesterol respectively, and are preferably prepared as liposomes having a diameter of about 100 nm. In a preferred embodiment, the plasmid includes a CMV promoter, a human IL-2 coding sequence, and a human growth hormone 3' untranslated region/poly(A) signal. In a preferred embodiment, the disease or condition is a cancer. In a preferred embodiment the composition is administered by injection.

In a related aspect, the invention provides a method for treatment of a mammalian condition or disease by administering a therapeutically effective amount of a composition for delivery and expression of a coding sequence in a mammal. The composition includes a cationic lipid and a neutral co-lipid, DOTMA and cholesterol respectively and a quantity of a DNA molecule (e.g., a plasmid) which includes a CMV promoter/enhancer sequence transcriptionally linked with a human IL-2 coding sequence, and a human growth hormone 3'-untranslated region/poly(A) signal.

As previously described, the DOTMA and DNA molecule are present in amounts so that the negative to positive charge ratio is about (1:0.5). Preferably the DOTMA and cholesterol are prepared as liposomes having a diameter of about 100 nm. In preferred embodiments the condition or disease is a cancer; preferably the composition is administered by injection.

Other features and advantages of the invention will be apparent from the following description of the preferred embodiments and from the claims.

BRIEF DESCRIPTION OF THE FIGURES

FIG. 5 is a table showing codon usage frequencies for highly expressed human genes.

DETAILED DESCRIPTION OF THE PREFERRED EMBODIMENTS

I. General

As described in the Summary above, this invention concerns expression systems for the delivery and expression of IL-2 coding sequences in mammalian cells, and formulations and methods for delivering such expression systems or other expression systems to a mammal.

Figure 1A:
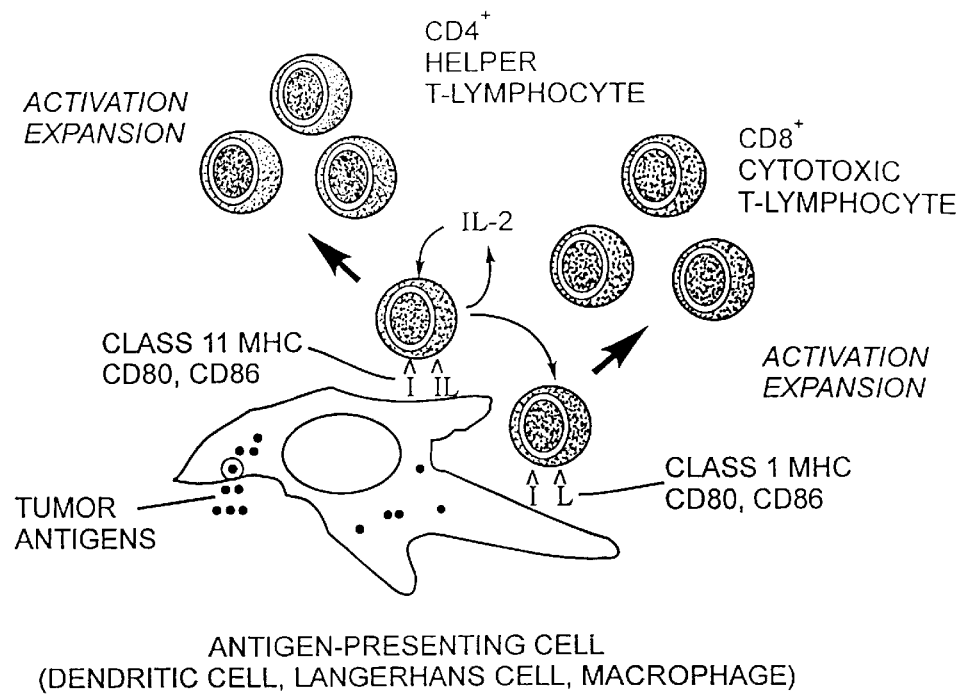
FIG. 1A–B provide schematic illustrations of the role of IL-2 in the expansion of activated helper T cells and cytotoxic T cells.
Figure 1B:
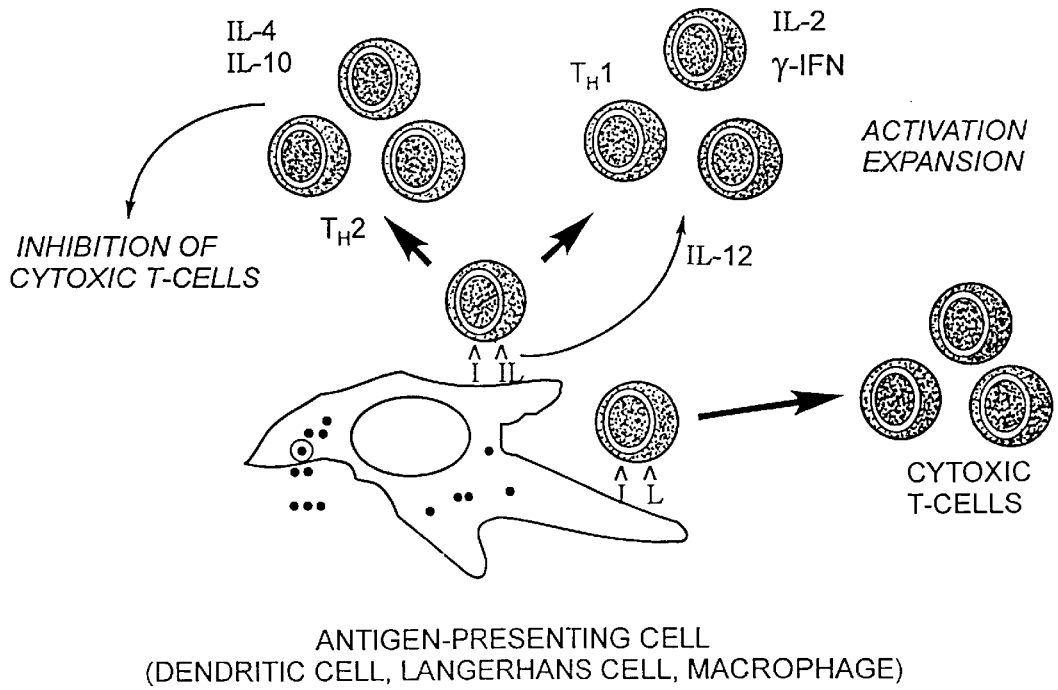

In part, the effects of such delivery can be understood from the effect of IL-2 in stimulating the proliferation of $T_H1$ helper T-cells and cytotoxic T-lymphocytes. The relationships as currently understood are shown in simplified schematic form in FIGS. 1A and 1B, illustrating the central role which antigen presenting cells (APCs) play in initiating and expanding the cellular immune response to cancer antigens. Thus, as shown in FIG. 1A, the response involves presentation of peptide (indicated by small dots) in association with Class I and Class II MHC, accompanied by co-stimulation by CD80(B7.1) and CD86(B7.2) to both helper and cytotoxic T-lymphocytes. The role of IL-2 in activating and expanding the antigen-specific responder T-cell populations also is shown. The right side of FIG. 1B provides a more detailed representation of the role of IL-12 produced by the APC, and IL-2 and IFN-γ produced by $T_H1$ cells in activating and expanding tumor-specific cytotoxic T-cells (CTL). The left side of FIG. 1B shows the expansion of $T_H2$ cells which produce IL-4 and IL-10 which in turn suppress the activation and expansion of $T_H1$ cells and CTL.

The relative presence of $T_H1$ and $T_H2$ cells can change over time as a tumor progresses. The process is influenced by the presence of cytokines which favor either $T_H1$, such as IL-2, IL-12, IFN-γ, and IFN-α, or $T_H2$, such as IL-4, IL-10, and TGF-β. Thus, biasing the system, such as by the expression of IL-2 from the plasmids and formulations described herein, to the expansion of $T_H1$ and CTL can stimulate and maintain an antitumor response.

Therefore, particular genetic constructs are described which includes nucleotide sequences coding for the human IL-2 subunits. Such a construct can beneficially be formulated and administered as described herein, utilizing the expression systems of this invention.

To allow convenient production of such plasmids, it is generally preferable that the plasmid be capable of replication in a cell to high copy number. Generally such production is carried out in prokaryotic cells, particularly including *Esherichia coli* (*E. coli*) cells. Thus, the plasmid preferably contains a replication origin functional in a prokaryotic cell, and preferably the replication origin is one which will direct replication to a high copy number.

It is also possible to utilize synthetic genetic elements in the plasmid constructs. As described below, these elements affect post-transcriptional processing in eukaryotic systems. Thus, the use of synthetic sequences allows the design of processing characteristics as desired for the particular application. Commonly, the elements will be designed to provide rapid and accurate processing.

For delivery of DNA encoding a desired expression product to a mammalian system, it is usually preferable to utilize a delivery system. Such a system can provide multiple benefits, notably providing stabilization to protect the integrity of the DNA, as well as assisting in cellular uptake.

In addition, as illustrated by an exemplary delivery system described herein, the non-DNA components of the formulation can contribute to an immune system enhancement or activation. As a result, components of a delivery system can be selected in conjunction with a particular gene product to enhance or minimize the immuno-stimulatory effect.

Immune system enhancement is described in another context in Yamamoto et al., 1994, *Microbiol. Immunol.* 38(10): 831–836. Oligo DNAs were described which stimulated the production of interferon and augmented the activity of NK cells; these effects were enhanced when lipofection was used.

Immunostimulatory effects are also described for certain nucleotide sequences. For example, Sato et al., 1996, *Science* 273: 352–354 describes the effects of vaccination with dsDNA having certain CpG containing sequences on the production of interferon-γ, interferon-β, and interleukin-12.

Rather than describing immunostimulatory effects, Parker et al., 1996, *Cancer Gene Ther.* 3: 175–185 describes an antitumor effect of an IL-2:DMRIE:DOPE formulation (DNA:lipid mass ratio of 5:1), indicating that the lipids inhibited DNA degradation and enhanced in vivo transfection as compared to naked DNA for intratumor injection. No IL-2 specific effect was shown for the injection into subcutaneous tumors (B-16 tumors in C57BL mice).

Similarly, Hofland & Huang, 1995, *Biochem. Biophys. Res. Comm.* 207: 492–494 described the anticancer effects of DNA:lipid formulations (DC-Chol, Lipofectin, or LipofectAMINE) injected in SCID mice bearing human ovarian carcinoma 2008 cells. The formulations enhanced survival time, but appeared to affect ascites cells but not the solid tumors.

It is demonstrated herein that, in addition to the effects of the choice of formulation components, for lipid-containing formulations, a cationic lipid:neutral co-lipid mixture (DOTMA:cholesterol) is effective for the purposes of transfection and immunostimulation. purposes. In addition, it is demonstrated that the manner of preparing the lipid combination and the relative amounts of lipid and DNA present are significant parameters determining the level of expression from the DNA coding regions and/or the in vivo physiological effect.

While these are specific effective examples, other components may be utilized in formulations containing the IL-2 expression vectors of the present invention to provide effective delivery and expression of human IL-2 or with other coding sequences for which manipulation of the activation of immune system components is desirable.

The selection of delivery system components and preparation methods in conjunction with the selection of coding sequences provides the ability to balance the specific effects of the encoded gene products and the immune system effects of the overall delivery system composition. This capacity to control the biological effects of delivery system formulation administration represents an aspect of the invention in addition to the IL-2 encoding constructs and specific formulations of delivery systems. Co-selection of the encoded gene product and the delivery system components and parameters provides enhanced desired effects rather than merely providing high level gene expression. In particular, such enhancement is described below for the antitumor effects of the exemplary IL-2 DNA:DOTMA:Chol compositions as seen in comparison to the IL-2:PVP formulations.

For systems in which the delivery system is selected to enhance the immuno-stimulatory effect, the antitumor effect can be greater than merely additive. Thus, for example, the antitumor effect of exemplary IL-2:DOTMA:Chol compositions is greater than merely the sum of the antitumor effects of naked IL-2 and DOTMA:Chol delivery systems containing empty plasmid. Enhancement of immuno-stimulatory effects is also desirable in other contexts, for example, for vaccine applications.

In contrast, for certain applications, it is preferable to select a delivery systems which minimizes the immune system effects. For example, it is often preferred that the immune system activation be minimized for compositions to be delivered to the lung in order to minimize lung tissue swelling.

A useful approach for selecting the delivery system components and preparation techniques for a particular coding sequence can proceed as follows, but is not limited to these steps or step order.

1. Select a particular genetic construct which provides appropriate expression in vitro.
2. Select delivery system components based on desired immunostimulatory effects and/or on in vivo physiological effect. Such effects can be tested or verified in in vivo model systems.
3. Select the other delivery system parameters consistent with the desired immuno-stimulatory effects and/or consistent with enhancing the desired in vivo physiological effect. Such parameters can, for example, include the amount and ratio of DNA to one or more other composition components, the relative amounts of non-DNA composition components, the size of delivery system formulation particles, the percent supercoiled DNA for circular dsDNA vectors, and the specific method of preparation of delivery system formulation particles. An example of delivery system preparation selection is selection of the method of preparation of liposomes for the exemplary IL-2:DOTMA:Chol formulations. The particular parameters relevant for specific types of formulations will be apparent or readily determined by testing.

The description below illustrates the selection of components and parameters in the context of IL-2 encoding constructs. However, it should be recognized that the approach is applicable to constructs containing a variety of other coding sequences.

II. Plasmid Construct Expression Systems

A. Plasmid Design and Construction

For the methods and constructs of this invention, a number of different plasmids were constructed which are useful for delivery and expression of sequences encoding human IL-2. Thus, these plasmids contain coding regions for IL-2, along with genetic elements necessary or useful for expression of those coding regions.

While these embodiments utilized IL-2 cDNA clones or partial genomic sequences from a particular source, those skilled in the art could readily obtain IL-2 coding sequences from other sources, or obtain a coding sequence by identifying a cDNA clone in a library using a probe(s) based on the published IL-2 coding and/or flanking sequences.

Figure 2:
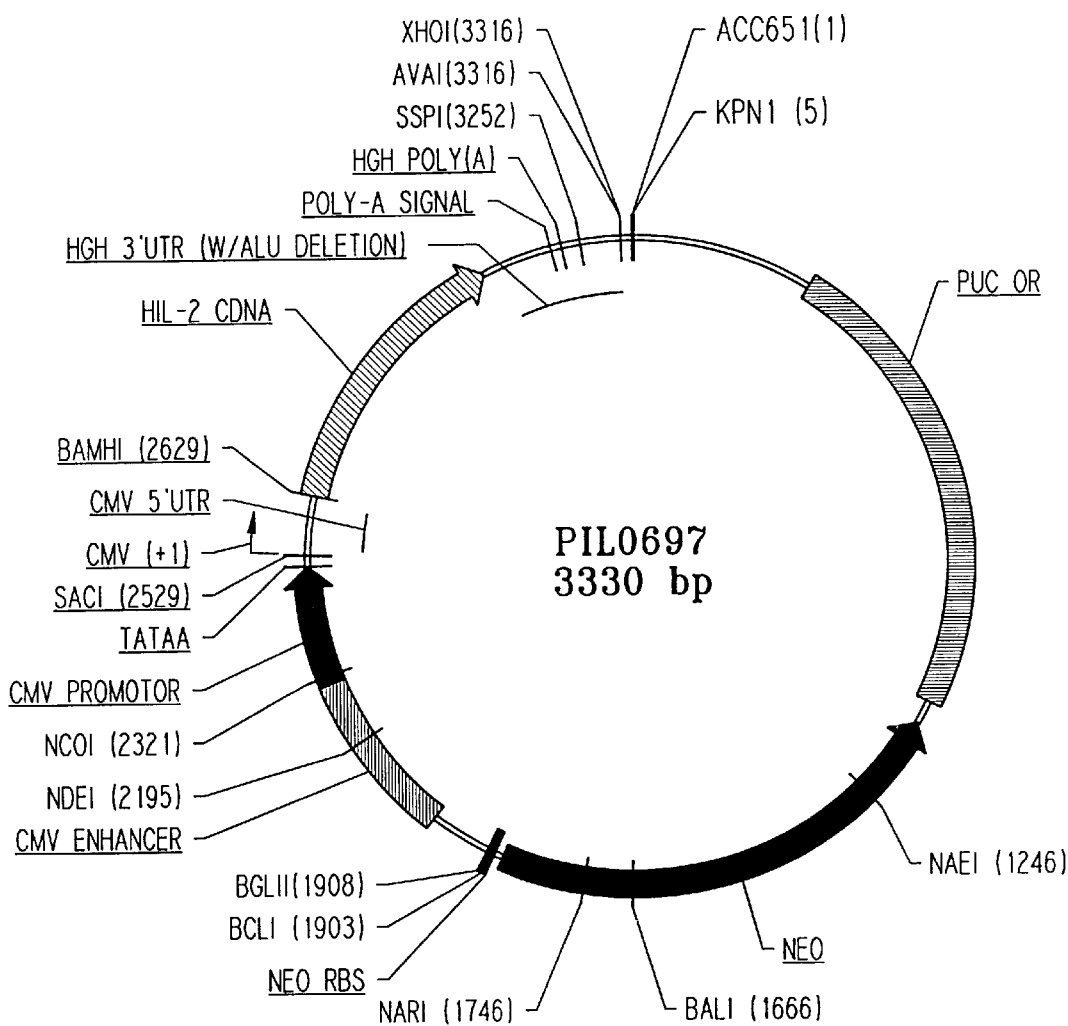
FIG. 2 is a schematic of an exemplary expression plasmid having an IL-2 coding sequence. The plasmid includes the bacterial elements, kanamycin resistance gene (kanR) and the plasmid origin of replication. The plasmid also include eukaryotic elements, CMV enhancer/promoter and 5' UTR, and human growth hormone 3' UTR/poly(A) signal.

Coding sequences for IL-2 were incorporated into an expression plasmid that contains eukaryotic and bacterial genetic elements, for example as shown schematically in FIG. 2. Eukaryotic genetic elements include the CMV immediate early promoter/enhancer and 5' UTR, and a human growth hormone 3' UTR/poly(A) signal), which influence gene expression by controlling the accuracy and efficiency of RNA processing, mRNA stability, and translation.

The human growth hormone 3' UTR is from a human growth hormone gene, and preferably includes a poly(A) signal. This sequence can be linked immediately following the natural translation termination codon for a cDNA sequence, genomic sequence, modified genomic sequence, or synthetic sequence coding for hIL-2.

An example of a human growth hormone 31 UTR/poly (A) signal is shown by the human growth hormone 3' UTR (nucleotides 1–100) and 3' flanking sequence (nucleotides 101–191; GenBank accession #J03071, HUMGHCSA) below. (SEQ ID NO. 4)

```
  1 GGGTGGCATCCCTGTGACCCCTCCCCAGTGCCTCTCCTGGCCCTGGAAGT

Poly (A)signal
 51 TGCCACTCCAGTGCCCACCAGCCTTGTCCTAATAAAATTAAGTTGCATCA

101 TTTTGTCTGACTAGGTGTCCTTCTATAATATTATGGGGTGGAGGGGGGTG

151 GTATGGAGCAAGGGGCAAGTTGGGAAGACAACCTGTAGGGC
```

The 5' and 3' UTR and flanking regions can be further and more precisely defined by routine methodology, e.g., deletion or mutation analysis or their equivalents., and can be modified to provide other sequences having appropriate transcriptional and translational functions.

A number of different constructs which incorporate human or murine IL-2 coding sequences are listed in Table I below.

TABLE I

| | Construct Name | Enhancer/ Promoter | 5'UTR | intron | coding |
|---|---|---|---|---|---|
| IL-2 Plasmids Expression Systems | | | | | |
| Mouse IL-2 cDNA | pIL0555A | CMV | CMV | none | mouse IL-2 cDNA |
| | pIL0719D | K6 1.2kb | CMV | none | mouse IL-2 cDNA |
| | pIL0735A, B | K6 1.2 kb | UT6 | synthetic (IVS9) | mouse IL-2 cDNA |
| | pIL0736A, B | K6 1.2 kb | K6 | K6, one intron in UTR | mouse IL-2 cDNA |
| Human IL-2 cDNA | pIL0618A | CMV | CMV | none | human IL-2 cDNA/Ncol |
| | pIL0629 | CMV | CMV | none | human IL-2 cDNA/Ncol |
| | pIL0633F | CMV | UT6 | synthetic (IVS8) | human IL-2 cDNA/Ncol |
| | pIL0674C | CMV | CMV | none | human IL-2 cDNA/BamHI/native CDS |
| | pIL0679A | CMV | UT6 | synthetic (IVS9) | human IL-2 cDNA/BamHI/native CDS |
| | pIL0680A | CMV | UT6 | synthetic (IVS9) | human IL-2 cDNA/BamHI/native CDS |
| | pIL0681A | CMV | UT6 | synthetic (IVS9) | human IL-2 cDNA/BamHI/native CDS |
| | pIL0697B | CMV | CMV | synthetic (IVS9) | human IL-2 cDNA/BamHI/native CDS |
| | pIL0751B | CMV | CMV | none | human IL-2 cDNA/BamHI/native CDS |
| Human IL-2 gene | pIL0578B | CMV | CMV | all natural introns | human IL-2 cDNA/Ncol |
| | pIL0566C | CMV | CMV | introns 2 and 3 truncated | human IL-2 cDNA/Ncol |
| | pIL0579 | CMV | CMV | intron 2 truncated | human IL-2 cDNA/Ncol |
| | pIL0634A | CMV | CMV | synth 9IVS8) plus trunc-introns 2 & 3 | human IL-2 cDNA/Ncol |
| | pIL0729A | CMV | CMV | introns 2 and 3 truncated | human IL-2 cDNA/BamHI/native CDS |
| | pIL0754F | CMV | CMV | intron 3, truncated | human IL-2 cDNA/BamHI/native CDS |

TABLE I-continued

IL-2 Plasmids Expression Systems

| Construct Name | Enhancer/ Promoter | 5'UTR | intron | coding |
|---|---|---|---|---|
| pIL0756 | CMV | CMV | introns 2 and 3 truncated | human IL-2 cDNA/BamHI/native CDS |
| pIL0747 | CMV | CMV | introns 2 and 3 truncated | human IL-2 cDNA/BamHI/native CDS |

Notes and abbreviations
CMV = cytomegalovirus
UTR = untranslated region
UT6 = synthetic 5' untranslated region
IVS = intervening sequence
synthetic intron (IVS9 vs. IVS8) = differ only by a single restriction site at the 3' END
2x synthetic polyA = two copies of a synethetic polyadenylation region
CDS = coding sequence
K6 1.2 kb = 1.2 kb upstream activating sequences of the mouse keratin 6 gene
UT6, IVS8 and 2x polyA were designed and constructed by S. Long and J. Nordstrom Of the constructs shown, pIL0697 is the preferred exemplary embodiment.

Figure 3:
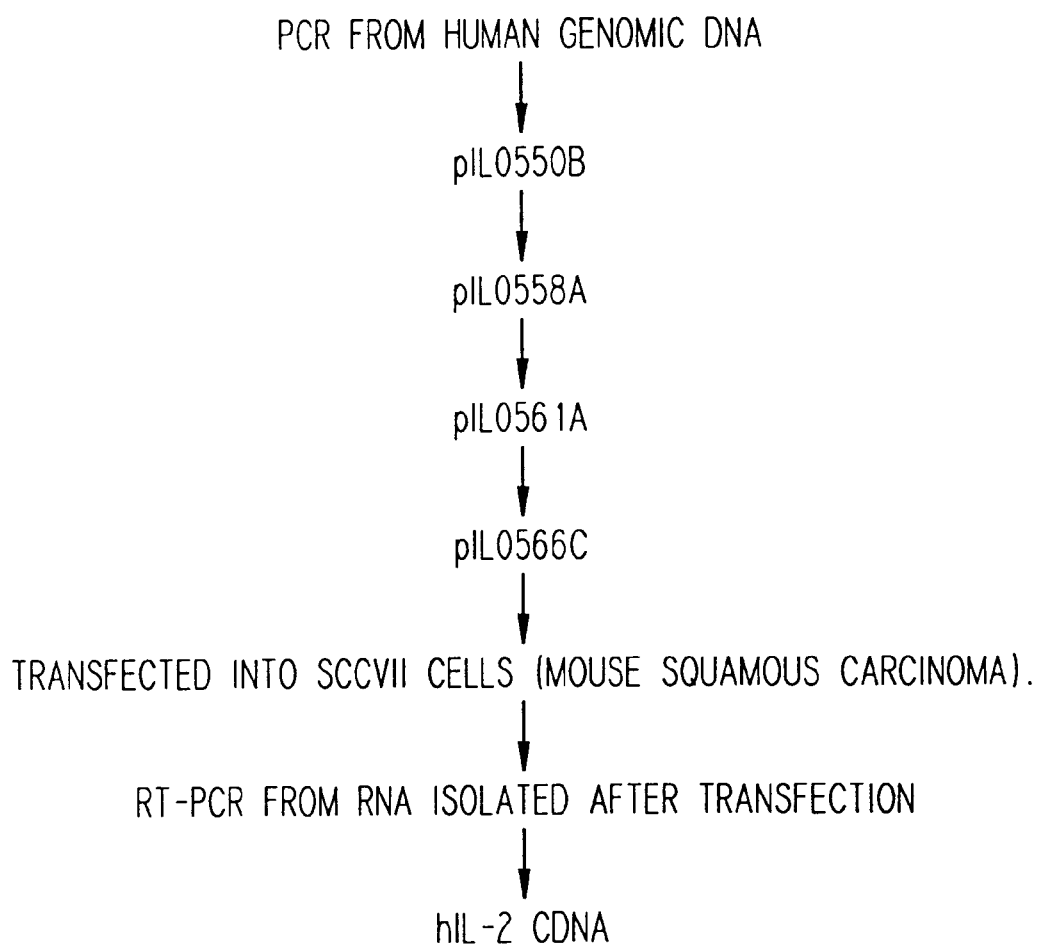
FIG. 3 is a diagrammatic representation of the PCR products and plasmids involved in generation of the hIL-2 cDNA which appears in the final hIL-2 construct pIL0697.
Figure 4:
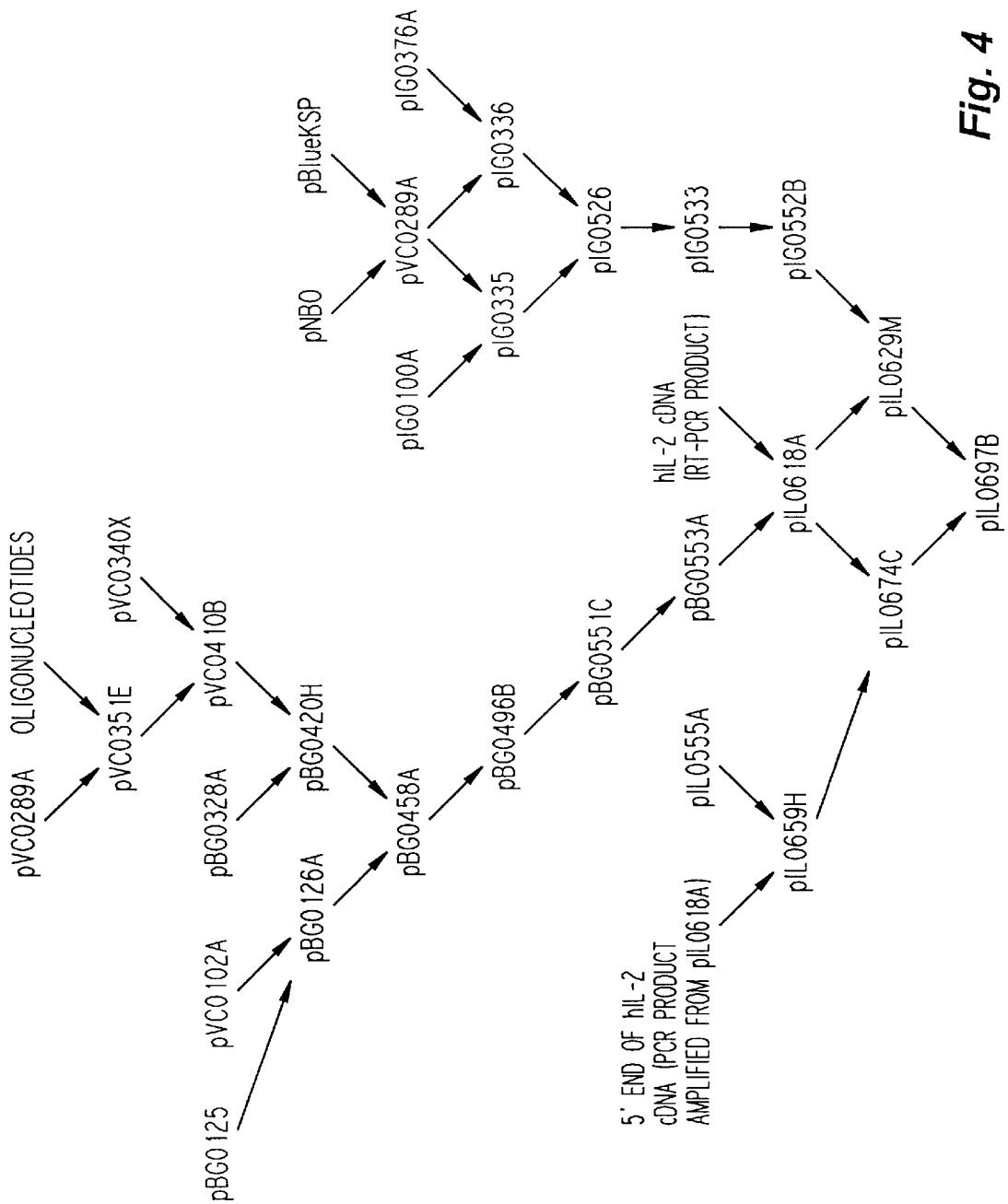
FIG. 4 is a diagrammatic representation of the plasmids involved in creation of pIL0697, the plasmid which directs expression of hIL-2 in the hIL-2 Gene Medicine. The sequences of the oligonucleotides shown are: ATGCGTCACGACGAGATCCTCGCCGTCGGNCATG and GCAGTGCTGCTCTAGGAGCGGCAGCC; these oligonucleotides were designed to inactivate an Nco I restriction site present in the 5' portion of the β-galactosidase coding region without altering the amino acid sequence of the β-galactosidase protein.

1. Construction of plasmid pIL0697: Plasmid Backbone, hIL-2 cDNA, Final Construct A diagrammatic representation of the PCR products and plasmids involved in creation of the final construct is shown below in FIGS. 3 and 4.

Plasmid pIL0697 contains the hIL-2 gene expression cassette in a plasmid containing a kanamycin-resistance (KanR) gene. The hIL-2 gene expression cassette of pIL0697 contains: 1) immediate early enhancer and promoter derived from cytomegalovirus (CMV); 2) the human interleukin-2 (hIL-2) cDNA; and 3) the human Growth Hormone (hGH) 3' untranslated region (3' UTR). The plasmid backbone is derived from pBluescript KS+(Stratagene) with 1) replacement of the bla gene (conferring ampicillin resistance) with the neo gene (conferring kanamycin-resistance) and 2) deletion of the f1 origin of replication.

Plasmid Backbone pVC0289 was created from pNEO (Pharmacia) and pBluescript KS+ (Stratagene) by ligating the 962 bp Bfa I (filled in with T4 DNA polymerase) to Dde I fragment of pNEO to the 1355 bp Fsp I to Dde I fragment of pBluescript KS+. pIG0100A and pIG0376A, the initial source of the hGH 3' UTR, were obtained from Dr. R. Schwartz at Baylor College of Medicine (Houston, Tex.). pIG0335 was constructed by ligating the 3472 bp Not I to Acc65I fragment of pIG0100A to the 2235 bp Not I to Acc65I fragment of pVC0289A. pIG0336 was constructed by ligating the 1918 bp Not I to Acc65I fragment of pIG0376A to the 2235 bp Not I to Acc65I fragment of pVC0289A. pIG0526 was constructed by ligating the 1132 bp BamHI to BamHI fragment of pIG0335 to the 3397 bp BamHI to BamHI fragment of pIG0336. pIG0533 was constructed by deleting the 472 bp Stu I fragment from pIG0526 and religating. pIG0552B was constructed by ligating the 395 bp Eco0109 (filled in with T4 DNA polymerase) to AccIII fragment of pIG0533 to the 3174 bp Xho I (filled in with T4 DNA polymerase) to AccIII fragment of pIG0533. The 211 bp Pst I to Acc65I fragment of pIG0552B contains the human growth hormone 3'-UTR that is part of the final construct.

The neo gene of pVC0289 contains a natural Nco I site. For ease of manipulation in subsequent cloning steps, the Nco I site in the neo gene was deleted ligating the oligonucleotides shown in FIG. 1 (which have Nco I and Sph I compatible overhangs) with the 2285 bp Nco I to Sph I fragment of pVC0289A, thereby generating pVC0351E. pBG0410B was constructed by ligating the 2287 bp Xho I (filled in with T4 DNA polymerase) to EcoRI fragment of pVC0351E to the 3999 bp Hind III (filled in with T4 DNA polymerase) to EcoRI fragment of pBG0340X. pBG0420H was constructed by ligating the 4827 bp Nar I (partial digestion; filled in with T4 DNA polymerase) to Cla I fragment of pBG0410B to the 965 bp EcoRI (filled in with T4 DNA polymerase) to Cla I fragment of pBG0328A.

pCMVβ (renamed pBG0125) and serves as tom Clontech and serves as the initial source of CMV immediate early enhancer and promoter. pBG0126A was constructed by ligating the 4529 bp EcoRI to Hind III fragment of pBG0125A to the 2843 bp EcoRI to Hind III fragment of pVC0102. pBG0458A was constructed by ligating the 663 bp Xho I (filled in with T4 DNA polymerase) to Spe I fragment of pBG0126A (containing the CMV enhancer and promoter) to the 5777 bp SnaBI to Spe I fragment of pBG0420H. For subsequent cloning steps, it was next useful to remove some undesired restriction enzyme sites, and this was accomplished by performing an Xho I partial digestion of pBG0458A and religating the resultant 6415 bp fragment, thereby generating pBG0496B. pBG0496B has an undesired EcoRI site which was removed by religating the 6379 bp Eco RI fragment of pBG0496B, generating pBG0551C. pBG0553A was constructed by religating the 6379 bp Xba I (partial digestion; filled in with T4 DNA polymerase) fragment of pBG0551C, so that the Xba I site at the 3' end of the β-galactosidase gene was now unique. pBG0553A contains the β-galactosidase coding sequence in a plasmid backbone containing the neo gene for growth selection and the CMV immediate early enhancer and promoter. The steps which remain are replacement of the β-galactosidase gene with hIL-2 cDNA and replacement of the bovine GH 3' UTR with the human GH 3' UTR. These steps are outlined below.

Human IL-2 cDNA

The coding sequence for hIL-2 which was used in generation of pIL0697 was derived from PCR amplification of human genomic DNA. The entire human IL-2 gene was PCR amplified from human genomic DNA (Promega) using primers designed from the GenBank sequence (HUMIL2; accession J00264). This PCR product was cloned into pCRII (Invitrogen) to make pIL0550B. pIL0550B was then modified by partial deletion of intron 2 using Cla I and Hinc II (both filled in with T4 DNA polymerase), to make pIL0558A. pIL0558A was modified by partial deletion of intron 3 using Mun I and BsmBI (both filled in with T4 DNA polymerase) to make pIL0561A. pIL0566C was constructed by ligating the 1765 bp BamHI to EcoRV fragment of pIL0561A to the 2936 bp Xba I (filled in with T4 DNA polymerase) to the BamHI fragment of pBG0553A. pIL0566C was transfected into SCCVII cells (mouse squamous cell carcinoma) and RNA was isolated. The human IL-2 cDNA was amplified from this RNA by RT-PCR with appropriately-designed primers. The second codon was modified to create an Nco I site. (This codon was later changed back to the naturally-occurring hIL-2 codon and is not present in the final construct pIL0697. This conversion is detailed in the construction of pIL0659H.) The hIL-2 cDNA RT-PCR product was digested with Bcl I (filled in with T4 DNA Polymerase) and BamHI (both sites present in the RT-PCR product but outside of the hIL-2 coding region), and the fragment cloned into the 2936 bp Xba I (filled in with T4 DNA polymerase) to BamHI fragment of pBG0553A to make pIL0618A. The second codon of the hIL-2 coding region was changed back to the naturally occurring codon by PCR using pIL0618A as the template DNA. Using appropriately-designed primers, a PCR product containing the 5' end of the hIL-2 cDNA with naturally-occurring second codon was generated and digested with BamHI (site present on the PCR primer) and Xba I and ligated to the 2937 bp BamHI to Xba I fragment of pIL0555A, to make pIL0659H. The 232 bp Xba I to Xba I fragment of pIL0618A, containing the 3' end of the hIL-2 cDNA, was ligated to the 3175 bp Xba I-digested pIL0659H to generate pIL0674C. pIL0674C contains the entire hIL-2 cDNA with naturally-occurring sequence.

Final Construct pIL0629M was constructed by ligating the 211 bp Pst I to Acc65I fragment (containing the hGH 3'-UTR) of pIG0552B with the 3158 bp Pst I (partial digestion) to Acc65I fragment of pIL0618A. pIL0697B was constructed by ligating the 231 bp Xba I to Acc65I fragment of pIL0629M with the 3098 bp Acc65I to Xba I (partial digestion) fragment of pIL0674C.

Cloning and Establishment of Recombinant Cell Lines 50 pg of pIL0697 DNA was added to 50 μL of DHFα Max Efficiency Competent cells (Gibco BRL/Life Technologies), and incubated on ice for 30 minutes in a sterile Falcon 2059 tube. A heat shock was applied by incubating at 42° C. for 45 seconds; 450 μL of SOC medium (Gibco BRL/Life Technologies) was then added and the mixture was incubated at 37° C. with shaking at 200 rpm. After 1 hour, 5 μL of the transformation mixture was mixed with 200 μL of SOC medium and plated on an LB agar+kanamycin (100 μg/mL) plate. The plate was inverted and incubated at 37° C. for approximately 15 hours as described in SOP 0108. This plate was then used in preparation of a master cell bank.

B. Synthetic Genetic Elements

In some embodiments, some or all of the genetic elements can be synthetic, derived from synthetic oligonucleotides, and thus are not obtained directly from natural genetic sequences. These synthetic elements are appropriate for use in many different expression vectors.

A synthetic intron is designed with splice sites that ensure that RNA splicing is accurate and efficient. A synthetic 3' UTR/poly(A) signal is designed to facilitate mRNA 3' end formation and mRNA stability. A synthetic 5' UTR is designed to facilitate the initiation of translation. The design of exemplary synthetic elements is described in more detail below.

1. Summary of Synthetic Element Features Exemplary synthetic 5' UTR, intron, and 3' UTR/poly(A) signal have the general features shown below:

5' UTR Short. Lack of secondary structure. Kozak sequence. Site for intron insertion.

Intron 5' splice site sequence matches consensus. 5' splice site sequence is exactly complementary to 5' end of U1 snRNA. Branch point sequence matches consensus. Branch point sequence is complementary to U2 snRNA. 3' splice site matches consensus. Polypyrimidine tract is 16 bases in length and contains 7 consecutive T's. (The tract preferably contains at least 5 consecutive T's.) Contains internal restriction enzyme sites. BbsI cleaves at the 5' ss, EarI cleaves at the 3' ss.

3' UTR/Poly(A) Based on rabbit β-globin 3' UTR/poly(A) signal. Consists of two poly(A) signals in tandem.

2. Features of the Synthetic 5' UTR (UT6):

The 5' untranslated region (5' UTR) influences the translational efficiency of messenger RNA, and is therefore an important determinant of eukaryotic gene expression. The synthetic 5' UTR sequence (UT6) has been designed to maximize the translational efficiency of mRNAs encoded by vectors that express genes of therapeutic interest.

The sequence of the synthetic 5' UTR (UT6) is shown below. The Kozak sequence is in boldface and the initiation codon is double underlined. The location of the intron (between residues 48 and 49) is indicated by the filled triangle and the sequences that form the exonic portion of consensus splice sites are single underlined. The restriction sites for HindIII and NcoI are overlined. (SEQ ID NO. 5)

```
       HindIII                                            ▼    NcoI
AAGCTTACTCAACACAATAACAAACTTACTTACAATCTTAATTAACAGGCCACCATGG
```

The 5' untranslated region (5' UTR), located between the cap site and initiation codon, is known to influence the efficiency of mRNA translation. Any features that influence the accessibility of the 5' cap structure to initiation factors, the binding and subsequent migration of the 43S preinitiation complex, or the recognition of the initiation codon, will influence mRNA translatability. An efficient 5' UTR is expected to be one that is moderate in length, devoid of secondary structure, devoid of upstream initiation codons, and has an AUG within an optimal local context (Kozak, 1994, *Biochimie* 76: 815–821; Jansen et al., 1994). A 5' UTR with these characteristics should allow efficient recognition of the 5' cap structure, followed by rapid and unimpeded ribosome scanning by the ribosome, thereby facilitating the translation initiation process.

The sequence of the synthetic 5' UTR was designed to be moderate in length (54 nucleotides (nts)), to be deficient in G but rich in C and A residues, to lack an upstream ATG, to place the intended ATG within the context of a optimal Kozak sequence (CCACCATGG), and to lack potential secondary structure. The synthetic 5' UTR sequence was also designed to lack AU-rich sequences that target mRNAs to be rapidly degraded in the cytoplasm.

Experiments have demonstrated that introns increase gene expression from cDNA vectors, and that introns located in the 5' UTR are more effective than ones located in the 3' UTR (Huang and Gorman, 1990, *Mol. Cell. Biol.* 10: 1805–1810; Evans and Scarpulla, 1989, *Gene* 84: 135–142; Brinster et al., 1988, *Proc. Natl. Acad. Sci. USA* 85: 836–840; Palmiter et al., 1991, *Proc. Natl. Acad. Sci. USA* 88: 478–482; Choi et al., 1991, *Mol. Cell. Biol.* 11: 3070–3074). Accordingly, the synthetic 5' UTR sequence was designed to accommodate an intron with consensus splice site sequences. The intron may, for example, be located between residues 48 and 49 (See intron sequence structure below). The CAG at position 46–48 is the exonic portion of a consensus 5' splice site. The G at position 49 is the exonic portion of a consensus 3' splice site.

To facilitate cloning manipulations, the synthetic 5' UTR sequence was designed to begin with a HindIII site and terminate with a NcoI site.

3. Features of the Synthetic Intron

RNA splicing is required for the expression of most eukaryotic genes. For optimal gene expression, RNA splicing must be highly efficient and accurate. A synthetic intron, termed OPTIVS8B, was designed to be maximally efficient and accurate.

The structure of the exemplary synthetic intron, OPTIVS8 is shown below. Sequences for the 5' splice site (5' ss), branch point (bp), and 3' splice site (3' ss) are double underlined. The recognition sequences for the restriction enzymes BbsI and EarI are overlined. The cleavage site for BbsI corresponds to the 5' ss, and the cleavage site for EarI corresponds to the 3' ss.

sequence was adjusted to contain 7 consecutive T residues. This feature was included because Roscigno et al. (1993) demonstrated that optimal splicing requires the presence of at least 5 consecutive T residues in the polypyrimidine tract.

Splicing in vitro is generally optimal when introns are >80 nts in length (Wieringa, et al., 1984; Ulfendahl et al., 1985, *Nucl. Acids Res.* 13: 6299–6315). Although many introns may be thousands of bases in length, most naturally occurring introns are 90–200 nt in length (Hawkins, 1988, *Nucl. Acids Res.* 16: 9893–9908). The length of the synthetic intron (118 nts) falls within this latter range.

OPTIVS8B was designed with three internal restriction enzyme sites, BbsI, NheI, and EarI. These restriction sites facilitate the screening and identification of genes that contain the synthetic intron sequence. In addition, the BbsI and EarI sites were placed so that their cleavage sites exactly correspond to the 5' ss (BbsI) or 3' ss (EarI). The sequence of the polypyrimidine tract was specifically designed to accommodate the EarI restriction site. Inclusion of the BbsI and EarI sites at these locations is useful because they permit

```
      5'ss                          bp                      3'ss
       |     BbsI                    |           EarI         |
5' CAG GTAAGTGTCTTC---(77)---TACTAACGGTTCTTTTTTTCTCTTCACAG G 3'

(SEQ ID NO. 6)                                (SEQ ID NO. 7)
```

The 5' splice site (5' ss) sequence matches the established consensus sequence, MAG ↓ GTRAGT, where M=C or A, and R=G or A. Since the mechanism of splicing involves an interaction between the 5' ss of the pre-mRNA and U1 snRNA, the 5' ss sequence of OPTIVS8B was chosen to be exactly complementary to the 5' end of U1 snRNA. 1

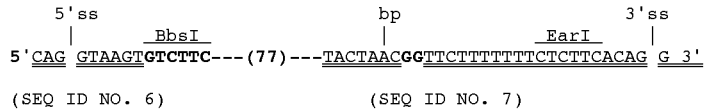

In mammals, the consensus sequence for branch points (YNYTR<u>A</u>Y, where Y=C or T, R=A or G, N=any base, and the underlined A residue is the actual branch point) is very ambiguous. Since the mechanism of splicing involves an interaction between the branch point (bp) of the pre-mRNA and U2 snRNA, the branch point sequence of OPTIVS8B was chosen to maximize this interaction. (Note that the branch point itself is bulged out). The chosen sequence also matches the branch point sequence that is known to be obligatory for pre-mRNA splicing in yeast. The branch point is typically located 18–38 nts upstream of the 3' splice site. In OPTIVS8B, the branch point is located 24 nts upstream from the 3' splice site. 1

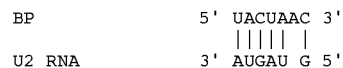

The sequence of the 3' splice site (3' ss) matches the established consensus sequence, $Y_{11}NYAG \downarrow G$, where Y=C or T, and N=any base. In 3' splice sites, the polypyrimidine tract ($Y_{11}$) is the major determinant of splice site strength. For optimal splice site function in OPTIVS8B, the length of the polypyrimidine tract was extended to 16 bases, and its the intron to be precisely deleted from a gene. They also permit the generation of an "intron cassette" that can be inserted at other locations within a gene.

The 77 bases between the BbsI site and the branch point sequence are random in sequence, except for the inclusion of the NheI restriction site.

4. Features of the Synthetic 3' UTR/poly(A) Signal

The 3' ends of eukaryotic mRNAs are formed by the process of polyadenylation. This process involves site specific site RNA cleavage, followed by addition of a poly(A) tail. RNAs that lack a poly(A) tail are highly unstable. Thus, the efficiency of cleavage/polyadenylation is a major determinant of mRNA levels, and thereby, of gene expression levels. 2XPA1 is a synthetic sequence, containing two efficient poly(A) signals, that is designed to be maximally effective in polyadenylation.

A poly(A) signal is required for the formation of the 3' end of most eukaryotic mRNA. The signal directs two RNA processing reactions: site-specific endonucleolytic cleavage of the RNA transcript, and stepwise addition of adenylates (approximately 250) to the newly generated 3' end to form the poly(A) tail. A poly(A) signal has three parts: hexanucleotide, cleavage site, and downstream element. The hexanucleotide is typically AAUAAA and cleavage sites are most frequently 3' to the dinucleotide CA (Sheets et al., 1987). Downstream elements are required for optimal poly (A) signal function and are located downstream of the cleavage site. The sequence requirement for downstream elements is not yet fully established, but is generally viewed as UG- or U-rich sequences (Wickens, 1990; Proudfoot, 1991, *Cell* 64: 671–674; Wahle, 1992, *Bioessays* 14: 113–118; Chen and Nordstrom, 1992, *Nucl. Acids Res.* 20: 2565–2572).

Naturally occurring poly(A) signals are highly variable in their effectiveness (Peterson, 1992). The effectiveness of a particular poly(A) signal is mostly determined by the quality of the downstream element. (Wahle, 1992). In expression vectors designed to express genes of therapeutic interest, it is important to have a poly(A) signal that is as efficient as possible.

Poly(A) efficiency is important for gene expression, because transcripts that fail to be cleaved and polyadenylated are rapidly degraded in the nuclear compartment. In fact, the efficiency of polyadenylation in living cells is difficult to measure, since nonpolyadenylated RNAs are so unstable. In addition to being required for mRNA stability, poly(A) tails contribute to the translatability of mRNA, and may influence other RNA processing reactions such as splicing or RNA transport ((Jackson and Standart,1990, *Cell* 62: 15–24; Wahle, 1992).

Some eukaryotic genes have more than one poly(A) site, implying that if the cleavage/polyadenylation reaction fails to occur at the first site, it will occur at one of the later sites. In COS cell transfection experiments, a gene with two strong poly(A) sites yielded approximately two-fold more mRNA than one with a single strong poly(A) site (Bordonaro, 1995). These data suggest that a significant fraction of transcripts remain unprocessed even with a single "efficient" poly(A) signal. Thus, it may be preferable to include more than one poly(A) site.

The sequence of the exemplary synthetic poly(A) signal is shown below. The sequence is named 2XPA. The hexanucleotide sequences and downstream element sequences are double underlined, and the two poly(A) sites are labeled as pA#1 and pA#2. Convenient restriction sites are overlined. The entire 2XPA unit may be transferred in cloning experiments as a XbaI-KpnI fragment. Deletion of the internal BspHI fragment results in the formation of a 1XPA unit. (SEQ ID NO. 8)

first poly(A) signal containing fragment, and a unique KpnI site at the 3' end of the second poly(A) signal containing fragment.

C. IL-2 Coding Sequences

The nucleotide sequence of a natural human IL-2 coding sequences is known, and is provided below, along with a synthetic sequence which also codes for human IL-2.

In some cases, instead of the natural sequence coding for IL-2, it is advantageous to utilize synthetic sequences which encode IL-2. Such synthetic sequences have alternate codon usage from the natural sequence, and thus have dramatically different nucleotide sequences from the natural sequence. In particular, synthetic sequences can be used which have codon usage at least partially optimized for expression in a human. The natural sequences do not have such optimal codon usage. Preferably, substantially all the codons are optimized.

Optimal codon usage in humans is indicated by codon usage frequencies for highly expressed human genes, as shown in FIG. 5. The codon usage chart is from the program "Human_High.cod" from the Wisconsin Sequence Analysis Package, Version 8.1, Genetics Computer Group, Madison, Wis. The codons which are most frequently used in highly expressed human genes are presumptively the optimal codons for expression in human host cells, and thus form the basis for constructing a synthetic coding sequence. An example of a synthetic IL-2 coding sequence is shown as the bottom sequence in the table below.

However, rather than a sequence having fully optimized codon usage, it may be desirable to utilize an IL-2 encoding sequence which has optimized codon usage except in areas where the same amino acid is too close together or abundant to make uniform codon usage optimal.

In addition, other synthetic sequences can be used which have substantial portions of the codon usage optimized, for

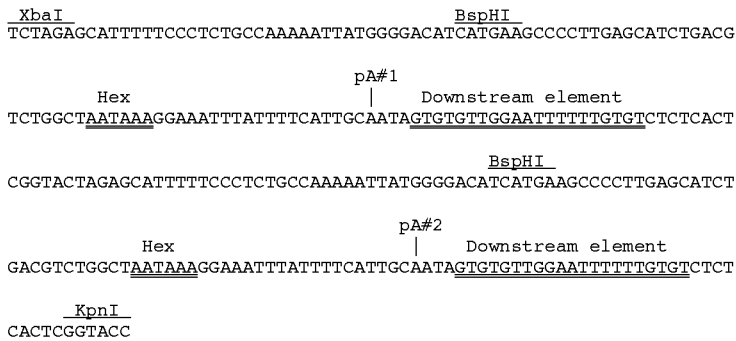

The sequence of the synthetic poly(A) site shown above is based on the sequence of the rabbit β-globin poly(A) signal, a signal that has been characterized in the literature as strong (Gil and Proudfoot, 1987, *Cell* 49: 399–406; Gil and Proudfoot, 1984, *Nature* 312: 473–474). One of its key features is the structure of its downstream element, which contains both UG- and U-rich domains.

A double-stranded DNA sequence corresponding to the 1XPA sequence was constructed from synthetic oligonucleotides. Two copies of the 1XPA sequence were then joined to form the 2XPA sequence. The sequences were joined in such as way as to have a unique XbaI site at the 5' end of the example, with at least 50%, 70%, 80% or 90% optimized codons as compared to a natural coding sequence. Other particular synthetic sequences for IL-2 can be selected by reference to the codon usage chart in FIG. 5. A sequence is selected by choosing a codon for each of the amino acids of the polypeptide sequences. DNA molecules corresponding to each of the polypeptides can then by constructed by routine chemical synthesis methods. For example, shorter oligonucleotides can be synthesized, and then ligated in the appropriate relationships to construct the full-length coding sequences.

TABLE II

HOMOLOGY OF WILD TYPE AND OPTIMIZED IL-2

| | |
|---|---|
| Gap Weight: 5.000 | Average Match: 1.000 |
| Length Weight: 0.300 | Average Mismatch: -0.900 |
| Quality: 235.9 | Length: 462 |
| Ratio: 0.511 | Gaps: 0 |
| Percent Similarity: 74.242 | Percent Identity: 74.242 |
| TOP: WILD TYPE | SEQ ID NO. 1 |
| BOTTOM: OPTIMIZED | SEQ ID NO. 2 |

```
 639 ATGTACAGGATGCAACTCCTGTCTTGCATTGCACTAAGTCTTGCACTTGT 688
     |||||| | ||||| || |||  ||||| || || || || || || ||
   1 ATGTACCGCATGCAGCTGCTGAGCTGCATCGCCCTGAGCCTGGCCCTGGT 50

689 CACAAACAGTGCACCTACTTCAAGTTCTACAAAGAAAACACAGCTACAAC 738
     || ||||| || || ||      ||   || |||||| || ||||| || |
  51 GACCAACAGCGCCCCCACCAGCAGCAGCACCAAGAAGACCCAGCTGCAGC 100

739 TGGAGCATTTACTGCTGGATTTACAGATGATTTTGAATGGAATTAATAAT 788
     |||||||  | ||||||||  | ||||||||| |||| || || || ||
 101 TGGAGCACCTGCTGCTGGACCTGCAGATGATCCTGAACGGCATCAACAAC 150

789 TACAAGAATCCCAAACTCACCAGGATGCTCACATTTAAGTTTTACATGCC 838
     |||||||| ||||| || ||| | ||||| || || ||||| ||||||||
 151 TACAAGAACCCCAAGCTGACCCGCATGCTGACCTTCAAGTTCTACATGCC 200

839 CAAGAAGGCCACAGAACTGAAACATCTTCAGTGTCTAGAAGAAGAACTCA 888
     |||||||||||| || |||||| || || ||||| || || || || |
 201 CAAGAAGGCCACCGAGCTGAAGCACCTGCAGTGCCTGGAGGAGGAGCTGA 250

889 AACCTCTGGAGGAAGTGCTAAATTTAGCTCAAAGCAAAAACTTTCACTTA 938
     | || |||||||||| ||||| ||  | || || ||||| ||||| ||| |
 251 AGCCCCTGGAGGAGGTGCTGAACCTGGCCCAGAGCAAGAACTTCCACCTG 300

939 AGACCCAGGGACTTAATCAGCAATATCAACGTAATAGTTCTGGAACTAAA 988
     | |||| ||| | ||||||||| |||||||| ||  || ||||| || ||
 301 CGCCCCCGCGACCTGATCAGCAACATCAACGTGATCGTGCTGGAGCTGAA 350

989 GGGATCTGAAACAACATTCATGTGTGAATATGCTGATGAGACAGCAACCA 1038
     |||    || || || |||||||| || || || || |||| || ||||
 351 GGGCAGCGAGACCACCTTCATGTGCGAGTACGCCGACGAGACCGCCACCA 400

1039 TTGTAGAATTTCTGAACAGATGGATTACCTTTTGTCAAAGCATCATCTCA 1088
     | || || || |||||| | ||||| ||||| || || ||||||||||
 401 TCGTGGAGTTCCTGAACCGCTGGATCACCTTCTGCCAGAGCATCATCAGC 450

1089 ACACTGACTTGA 1100
     || ||||| |||
 451 ACCCTGACCTGA 462
```

It was determined that both the natural coding sequence and the synthetic coding sequence are translated to form the identical polypeptide, the sequence of which is shown in Table III below as the translation of the natural coding sequence (SEQ ID NO. 3).

TABLE III

TRANSLATION of: WILD TYPE IL-2

```
  1 MYRMQLLSCI ALSLALVTNS APTSSSTKKT QLQLEHLLLD LQMILNGINN

51 YKNPKLTRML TFKFYMPKKA TELKHLQCLE EELKPLEEVL NLAQSKNFHL

101 RPRDLISNIN VIVLELKGSE TTFMCEYADE TATIVEFLNR WITFCQSIIS

151 TLT*
```

III. Model Systems for Evaluation of IL-2 Constructs and Formulations

In accord with the concept of using IL-2 expressing plasmid constructs and formulations in anti-cancer treatment, murine model systems were utilized based on murine tumor cell lines. The line primarily used was S.C. VII/SF, which is a cell line derived from murine squamous cell carcinoma (S.C.).

Squamous cell carcinoma of the head and neck begins with the cells lining the oral and pharyngeal cavities. Clinical disease progresses via infiltration and spreads into the underlying tissues and lymphatics. The undifferentiated, in vivo passage tumor line S.C. VII/SF displays this typical growth pattern. In addition, its rapid growth rate provides a relatively short test period for individual experiments. Other murine tumor cell lines include another SCC line KLN-205 a keratinocyte line I-7 and a colon adenocarcinoma line MC-38.

An optimal model system preferably satisfies the criteria based on having tumor growth rate in vivo (i.e., tumors are ready for treatment in 4–10 days post implant), invasiveness, and local spread similar to those observed in clinical disease, and providing accessibility for experimental treatment. As indicated, the SCC DII/SF cell line was utilized as the primary model system cell line. This cell line typically grows rapidly, resulting in death of untreated syngeneic mice 14–17 days after tumor cell implantation.

This cell line can be utilized in a variety of ways to provide model system suitable for a variety of different tests. Four such possibilities are described below.

First, SCCVII cells can be utilized in cell culture to provide an in vitro evaluation of IL-2 expression construct and formulation characteristics, such as expression levels and cellular toxicities.

Second, the cells can be implanted subcutaneously in mice. This system can be utilized in tests in which accessibility of the implant site is beneficial. As an example, the method was utilized in evaluations of expression efficiencies based on the expression of chloramphenicol acetyltransferase (CAT).

Third, the cells can be implanted transcutaneously into the fascia of digastric muscle.

Fourth, the cells can be implanted transcutaneously into digrastric/mylohyoid muscles. The important features of models 3 and 4 are shown in the table below.

TABLE IV

Comparison of submandibular tumor models

| Feature | Mouse Tumor Model 3 | Mouse Tumor Model 4 |
|---|---|---|
| Tumor implant procedure | 2–4 × $10^5$ cells transcutaneously into fascia of digastric muscle | 5 × $10^5$ trnascutaneously into digastric/mylohyoid muscles |
| Tumor growth and invasiveness characteristics | Prominent submandibular bulge; invasion of digastric/mylohyoid muscles and lymphatics | More variable, invasion of digastric mylohyoid muscles and lymphatics |
| Treatment procedure (primary treatment) | Transcutaneous, needle inserted and moved within tumor to produce a 4 quadrant distribution of gene medicine | Lower jaw skin flap raised to expose tumor, needle inserted and moved within tumor to produce a 4 quadrant distribution of gene medicine |
| Days treated (post-implant) | Day 5, day 10 (both transcutaneously) | Day 5 (tumor exposed), day 8 (transcutaneously) |
| Measurement procedure | External calipering 2–3 × per week until death | First caliper when tumor exposed for treatment, second caliper at sacrifice |
| Advantages | Non-surgical, closed model allows larger experiments and more frequent treatments; Sacrifice unnecessary to caliper (= more time points) | Surgical, open model allows direct treatment of exposed tumor; Local inflammation from surgery may additionally stimulate immune response; More like clinical situation for protocol development |
| Disadvantages | Transcutaneous treatment is potentially less accurate and intensive; less like expected clinical treatments than surgical approaches | Labor intensive; Smaller, fewer experiments possible; Tumors deeper and more difficult to treat transcutaneously (for secondary treatments); Fewer treatments and caliperings possible |

The tumor size treated in the mouse models is generally 20–50 mm³. A 50 mm³ mouse tumor is approximately equivalent to 150 CC³ human tumor having an average diameter of about 6.6 cm. This tumor size is approximately 10-fold larger than the size proposed to be treated in the phase I clinical trials. This indicates that the mouse models are strongly biased towards over estimating the expected tumor burden in human patients.

IV. Formulations for In Vivo Delivery

A. General

While expression systems such as those described above provide the potential for expression when delivered to an appropriate location, it is beneficial to provide the expression system construct(s) in a delivery system which can assist both the delivery and the cellular uptake of the construct. Thus, this invention also provides particular formulations which include one or more expression system constructs (e.g., DNA plasmids as described above), a cationic lipid, a co-lipid (preferably a neutral co-lipid), and a carbohydrate agent to make the formulation iso-osmotic and isotonic.

In addition to the lipids and lipid combinations described herein for exemplary formulation embodiments, other lipids may be selected. As indicated in the Summary above, examples are described in Gao & Huang, 1995, Gene Therapy 2: 710–722 and are summarized in the table below. Chemical structures for these compounds are provided in FIG. 10.

mixed as a 50:50 mole percent ratio, then lyophilized. This lyophilized powder is the raw material from which the liposomes used in the hIL-2 exemplary formulations.

The lyophilized material is analyzed with respect to identity and composition, then rehydrated with sterile water for irrigation USP to allow liposome formation. The rehydrated material is microfluidized to generate a homogenous population of small liposomes. The microfluidized material is then 0.2 micron-filtered and analyzed with respect to composition, particle size, and sterility.

During the process of microfluidization, a source of ultrapure nitrogen gas (Air Liquide) is used to drive the air driven pressure system of the microfluidizer M110S (Microfluidics Corporation) unit, however, other microfluidizers could also be used. The lyophilized lipid mixture is allowed to come to room temperature, then sterile water for irrigation U.S.P., approximately 200 mL, is added. The mixture is allowed to rehydrate for approximately 1.5 hours before any further processing. Once rehydration is completed and a translucent homogeneous suspension is obtained, the liposomes are microfluidized. For this, a pressure of approximately 50,000 psi is applied to the microfluidizer unit and the sample is cycled through the chamber at least 10 times, which in turn produces a population of

| Cationic Liposome | Composition | Manufacturer | Probable biodegradability of cationic | Transfection Activity In vitro | Transfection Activity In vivo |
|---|---|---|---|---|---|
| A: Commercialized | | | | | |
| Lipofectin | DOTMA/DOPE=1:1(w/w) | GIBCO BRL | No | +++ | ++ |
| DOTAP | DOTAP | Boehringer Mannheim | Yes | +++ | ++ |
| TransfectAce | DDAB/DOPE=1:1(m/m) | GIBCO BRL | No | +++ | NA |
| LipofectAMINE | DOSPA/DOPE=1:1(w/w) | GIBCO BRL | Partial | ++++ | NA |
| Transfectam | DOGS | Promega | Partial | ++++ | +++ |
| B. Not commercialized | | | | | |
| CTAB | CTAB/DOPE=1:4(m/m) | | No | ++ | NA |
| $C_{12}$CluPhCnNa | $C_{12}$GluPhCnN | | Yes | +++ | NA |
| $C_{12}$GluCnN | $C_{12}$GluCnN | | Yes | +++ | NA |
| Lipopolylysine | Lipopolylysine/DOPE=1:8(m/m) | | Yes | +++ | NA |
| Cationic cholesterols | Cationic chol/DOPE=1:1(m/m) | | | Yes | +++ |
| DC-chol | DC-chol/DOPE=3:2(m/m) | | Yes | +++ | +++ |
| DMRIE | DMRIE/DOPE=1:1(m/m) | | NO | +++ | +++ |
| DOTMA/chol | DOTMA/cholesterol=1:1(m/m) | | No | +++ | NA |
| Lysyl-PE | Lysyl-PE/β-alanyl cholesterol=1:1(m/m) | | Yes | +++ | NA |

In composition in which lipids, such as DOTMA and cholesterol, are used, preferably, though not necessarily, the cationic lipid and the neutral co-lipid are formed into liposomes, such as by forcing the lipid and aqueous solution through a membrane with pores of a desired size or by microfluidization. The liposomes are combined with the DNA to form a DNA/lipid complex, which can then be administered to a mammal by a delivery method appropriate to the desired delivery site.

Formation of liposomes by microfluidization provides liposomes of discrete size, i.e., the size distribution is narrower than other preparation methods tested. This preparation method can, as an example, be performed as follows. For the exemplary DOTMA/chol formulations, the liposomes are composed of the cationic lipid DOTMA (1,2-di-O-octadecenyl-3-trimethylammonium-propane, chloride salt) and the uncharged colipid cholesterol mixed to give a 50:50 mole percent ratio. DOTMA and cholesterol are vesicles of reduced size. Following microfluidization, a sample is collected for an in-process particle check. After a predeterminied particle size is achieved, the material is removed and filtered through a 0.2 micron filter. At this point, the material may be diluted with sterile water for irrigation U.S.P. to achieve a desired concentration. The liposome solution was vialed under an overlay of Argon gas.

A description of the use of liposomes for gene transfer is provided in Szala et al., 1996, Gene Therapy 3: 1026–1031. In this report, cationic liposomes using DC-Chol/DOPE and DDAB/DOPE were used to transfer E. coli cytosine deaminase gene into melanoma tumors by direct injection.

As described below, the selection of non-DNA formulation components, the diameter and size distribution of the liposomes, and the DNA:cationic lipid charge ratio are significant parameters in determining the resulting level of expression.

An additional significant factor relating to the plasmid construct is the percentage of plasmids which are in a supercoiled (SC) form rather than the open circular (OC) form.

The in vivo effects of such formulations is particular notable in comparison with the in vivo effects of an alternative formulation which produced even higher levels of encoded product, i.e., a DNA:PVP formulation.

B. Evaluation of Effect of Selection of Formulation Components. Liposome Size. DNA:Cationic Lipid (−:+) Charge Ratio As indicated above, the parameters of formulation component selection, liposome size, and charge ratio were shown to be significant parameters in determining the level of expression and treatment efficacy observed when the formulated complexes were delivered.

The initial evaluation concerned the transfection and expression levels for compositions having different non-DNA components with a CMV-CAT reporter (plasmid with a cytomegalovirus promoter and a chloramphenicol acetyltransferase reporter gene). It was found that for transfection of tumors in vivo, both DNA in isotonic aqueous solution and DNA in 5% PVP produced high level of expression in comparison with formulations containing lipids. Of the lipid containing formulations, the combination of DOTMA and cholesterol produced higher levels of expression as compared to DOTMA/DOPE, DOTAP/chol, DOTAP/DOPE, and EDOPC. (DOTAP is 1,2-dioleoyl-3-trimethylammonium propane, and DOPE is 1,2-dioleoyl-glycero-3-phosphoethanolamine.)

Based on such results, the DNA:PVP and DNA:DOTMA:Chol formulations were further investigated for expression of IL-2 in tumors (tumor explants). In these DOTMA:Chol formulations, and other compositions containing cationic and neutral lipids, the cationic lipid and the neutral co-lipid are preferably present in approximately equimolar amounts. It was determined that the PVP containing formulations produced significantly higher hIL-2 expresssion levels in tumors than did the DOTMA:Chol containing formulations. Human IL-2 was detected using a monoclonal antibody (mAB) to human IL-2, allowing detection and quantitation in the presence of mIL-2.

Figure 6:
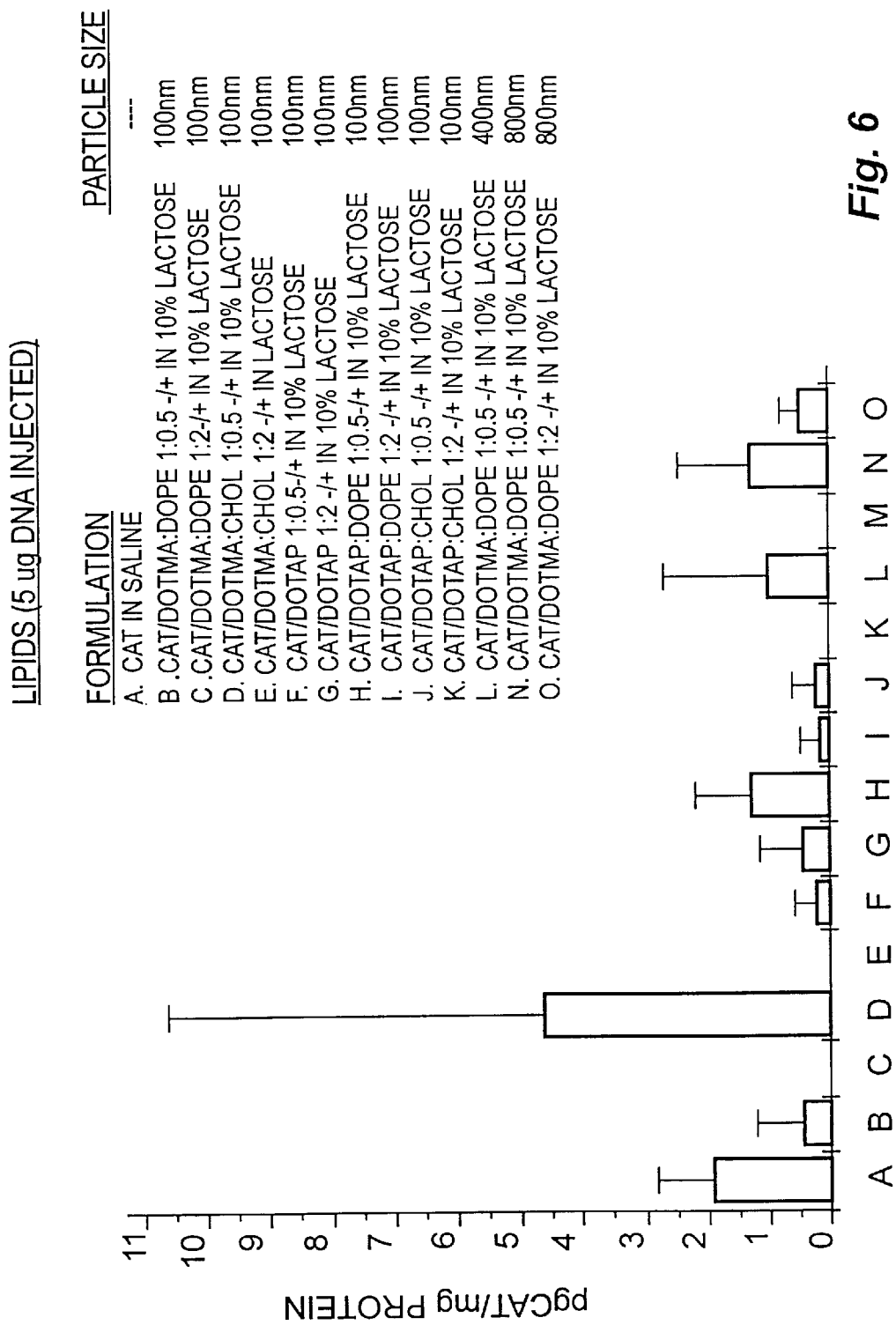
FIG. 6 is a graph showing the relative CAT expression levels of a number of different DNA:lipid delivery formulations in a murine tumor model.

For lipid containing formulations, the effects of lipid selection, DNA:lipid charge ratio, and liposome size on expression level in expression formulations were evaluated using Model 2, the subcutaneous implant model, based on ELISA detection of chloramphenicol acetyltransferase expressed from the plasmids in the formulations. Formulations containing 5 μg of DNA were injected into the tumor. The results are shown in FIG. 6, which shows that DOTMA:Chol prepared as 100 nm liposomes with a DNA:lipid negative to positive charge ratio of 1:0.5 produced the highest level of CAT expression of the combinations tested. As a result of these and similar results, this combination was chosen as the preferred formulation for further tests, and will be referred to as "the exemplary formulation". However, it is clear that other formulations can also provide useful expression.

The effectiveness of the DOTMA:Chol formulation identified above was confirmed by the determination of expression level of hIL-2 in transfected mouse tumors using mouse Model 2. For this analysis, at 8–10 hours post-treatment, tumors were removed and either processed for extraction of RNA or cultured as solid explants for analysis of protein secretion after 24–48 hours.

hIL-2 was detected using the PREDICTA™ hIL-2 ELISA kit from Genzyme. In two tests, approximately 4–6 pg of hIL-2 per tumor was detected at 24 and 48 hours after injection, while 0 pg hIL-2 was detected following injection with a formulation having the same non-DNA components but having CAT encoding plasmid rather than hIL-2 encoding plasmid.

C. Delivery and Expression

A variety of delivery methods can be used with the constructs and formulations described above, in particular, delivery by injection to the site of a tumor can be used. The submandibular tumor models utilized injection into four quadrants of the tumor being treated.

D. Anti-Cancer Efficacy of hIL-2 Formulations

The effects of the administration of the IL-2 DNA:PVP and IL-2 DNA:lipid formulations described above and others were evaluated using the S.C. VII mouse tumor models. Plasmid constructs as described above were incorporated in delivery formulations. In most tests, 12.5 μg of plasmid DNA was combined with DOTMA:chol (equimolar DOTMA:cholesterol prepared as 100 nm liposomes with the DNA and DOTMA in a 1:0.5 negative to positive charge ratio. The formulations were delivered by injection.

1. Comparison of efficacy of exemplary formulation vs. PVP-IL-2 plasmid and vs. adenovirus-IL-2 formulations: The anti-tumor efficacy of formulations containing hIL-2 or mIL-2 plasmid with DOTMA:Chol prepared as 100 nm liposomes, 1:0.5 (−/+) was compared to the efficacy of other formulations by comparing the tumor volume at time points following formulation injection. The initial evaluations used DNA encoding mIL-2 and showed that an exemplary formulation with 12.5 μg mIL-2 produced greater tumor inhibition than a formulation with 150 μg mIL-2 plasmid in 5% PVP and than an adenovirus-IL-2 vector. Quantitation was performed at days 0 and 8 following injection.

Figure 7:
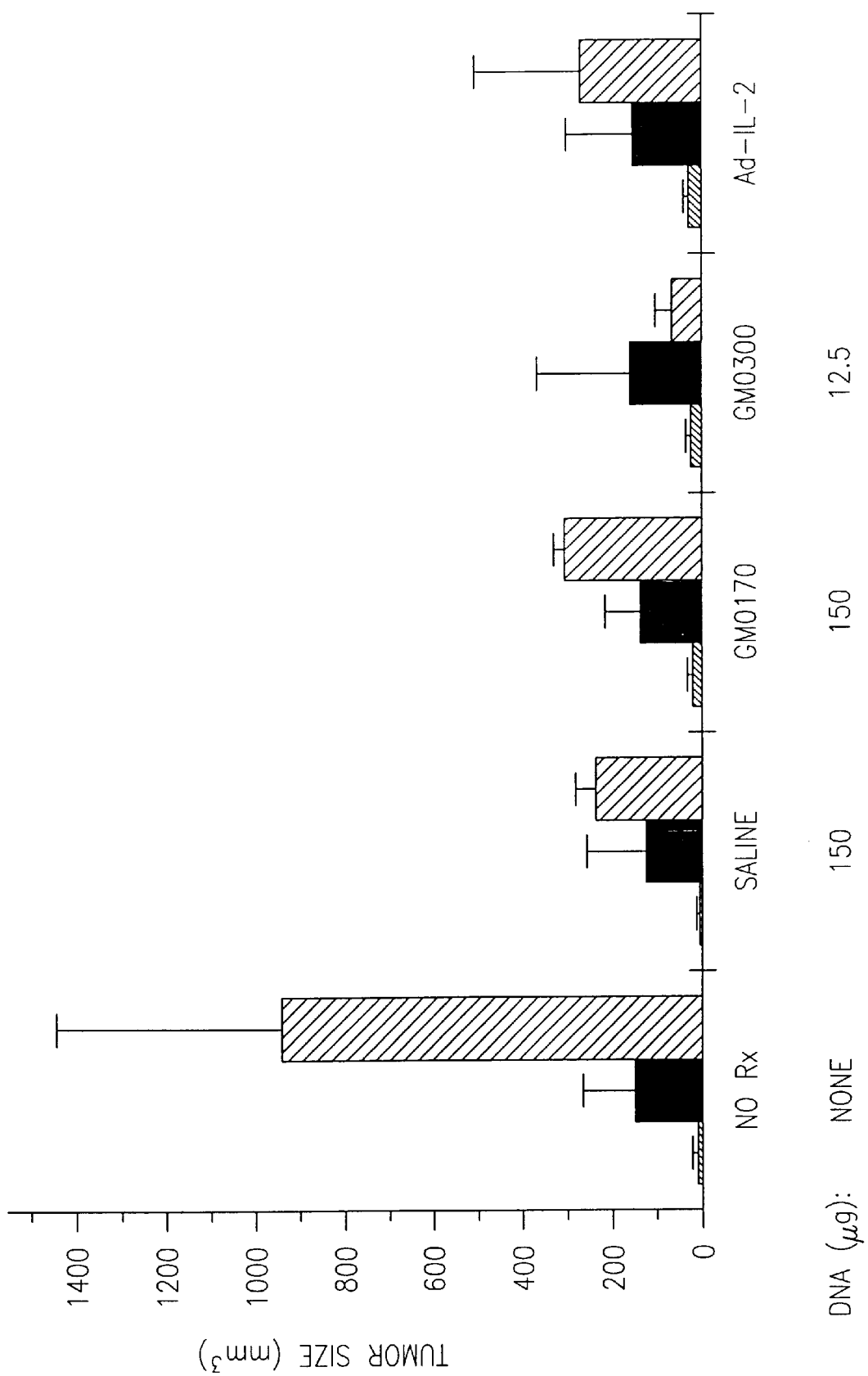
FIG. 7 is a bar graph showing the results of antitumor treatment in a murine tumor model by the effect on tumor volume. Tumors were injected with formulations which included DNA encoding hIL-2.

The results were confirmed with DNA encoding hIL-2. In these tests, quantitation was performed at days 0 and 5 following injection, and every two to four days thereafter until the experiment was complete. As shown in FIG. 7, the exemplary formulation resulted in dramatically smaller tumors at the last time point than injections of (1) >10 times the amount of the same plasmid with saline; (2) >10 the amount of the same plasmid with 5% PVP; and (3) an adenovirus-hIL-2 vector. Treatment with the exemplary formulation resulted in tumors of about 30 mm$^3$ at the last time point; by comparison untreated tumors were about 900 mm$^3$ at the same time point.

Results of this type suggested that formulations of IL-2 encoding DNA with DOTMA/Chol as described above (in particular the exemplary formulation) had enhanced antitumor efficacy as compared to the DNA/PVP formulations. Thus, the antitumor effect was seen to not depend only on the expression level of IL-2, but to also be a function of the non-DNA formulation components, with the effect being greater than merely additive. Anti-tumor efficacy was also observed for IL-2 plasmid formulated with a different cationic lipid, though at a different charge ratio than for DOTMA/chol.

2. Comparison of antitumor efficacy of different IL-2 plasmid constructs with DOTMA:Chol: The antitumor effects of delivery of several of the constructs listed in Table I above were tested in the mouse submandibular tumor model. Those constructs were the 612(empty plasmid), 566, 674, 679, 697, and 555. Tumor cells were implanted at day −5, and injections were performed on days 0 and 4. Injection of lactose and injection of the 612 empty plasmid resulted in tumors at the endpoint of approximately 900–1000 mm$^3$. Injection of formulations as described for the exemplary formulation, but each having 12.5 μg of one of the specified plasmids each resulted in reduced endpoint tumor size, with the sizes ranging from about 250–750 mm³.

Figure 8:
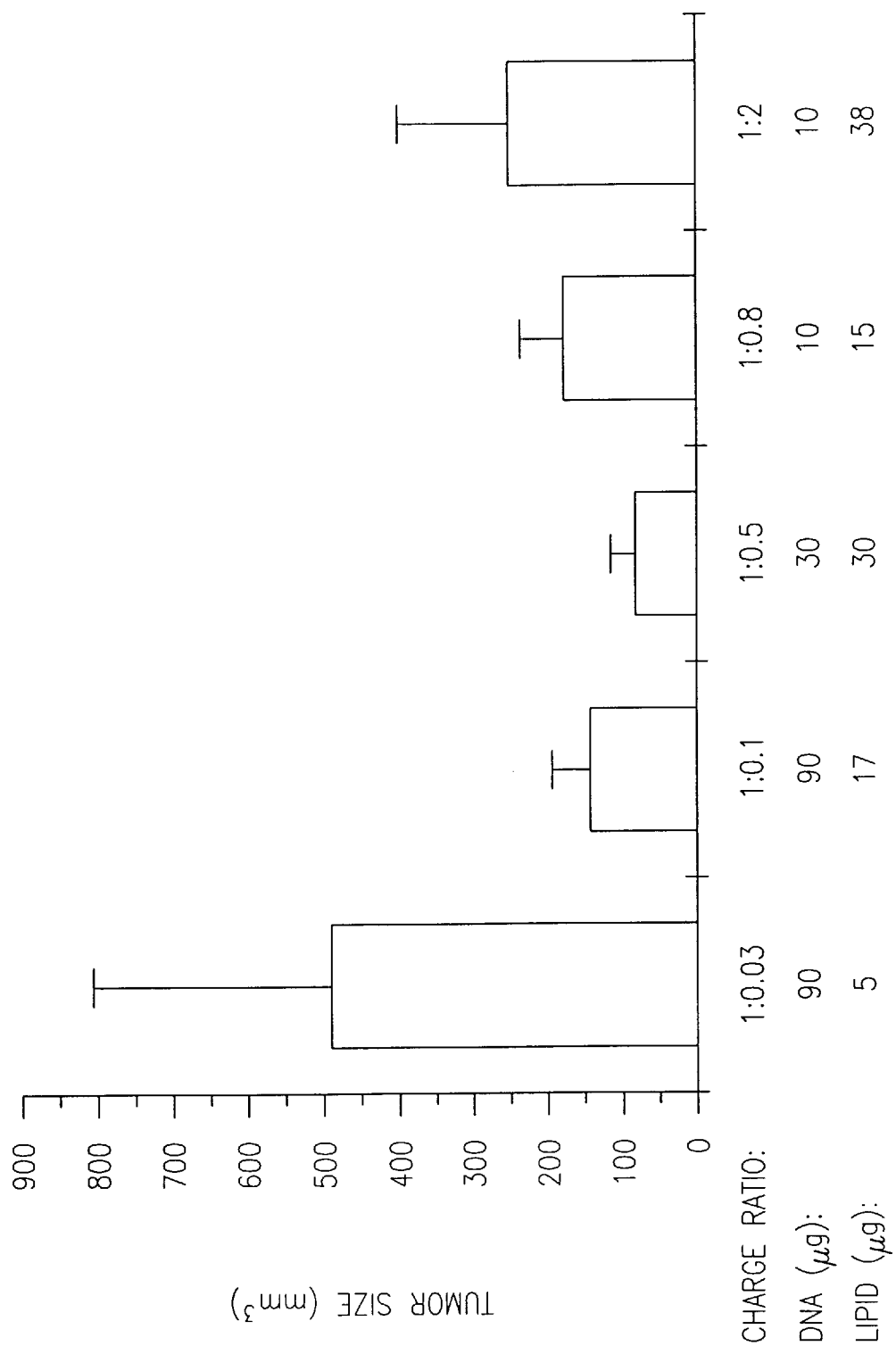
FIG. 8 is a bar graph illustrating for administration of formulations at approximately constant formulation particle size, IL-2 encoding formulations with DOTMA/Chol having a charge ratio of about 1:0.5 resulted in the greatest inhibition of tumor growth.

3. Comparisons of antitumor efficacy of formulations having differing charge ratios: The efficacy of formulations similar to the exemplary formulation, but containing differing amounts of DNA and cationic lipid, and therefore having differing charge ratios were also assessed. The charge ratios ranged from 1:0.03 to 1:2 (−/+). As shown in FIG. 8, the resulting tumor sizes in an S.C. submandibular tumor model was the lowest for the formulation in which the charge ratio was 1:0.5 (−/+).

4. Comparison of antitumor efficacy of IL-2 formulations with single injection vs. two injections: In a further test using a mouse submandibular tumor model, it was shown that the use of two injections (on days 0 and 4) was more effective than a single injection (on day 0) for both the exemplary construct and a murine IL-2 construct for tumors measured at day 8 (13 days after tumor cell implantation). For both IL-2 plasmids, the use of two injections resulted in tumors which had approximately one half the volume of the corresponding tumor following a single injection.

These results indicate that multiple injection dosing is more effective than single injection dosing. The most effective dosing frequency and dose number can be readily determined in model system tests, followed by small scale clinical trials, by routine methods.

E. Cytotoxic Activity of Tumor Specific Cytotoxic Cells in Spleen & Draining Lymph Nodes Following the injection of IL-2 plasmid containing formulations in mouse tumors in the tumor models described above, IL-2 mRNA was found in spleens and draining lymph nodes of treated animals. Evaluation of the tumor specific cytolytic activity of lymphocytes from these sites for animals treated with the IL-2 plasmid formulations showed that activity for treated animals was higher than for animals injected with formulations containing control plasmid lacking IL-2 coding sequences or with saline.

This analysis was performed using a standard $^{51}$Cr release assay. A greater cytotoxicity was observed against SCC VII/SF cells than against control Rif tumor cells.

In contrast to other systems where in vivo-derived effector cells must be re-stimulated in vitro to obtain good cytotoxic activity, these anti-tumor lymph nodes and splenocytes were tested directly in the cytotoxicity assay. The highest cytotoxicity was observed with the lymph node effector cells, where 60–70% cytotoxicity was obtained at a 100:1 effector:target cell ratio with the hIL-2 groups (hIL-2 plasmid administered by injection as the exemplary formulation).

It was observed that in the lymph nodes, the formulation complex containing DNA without hIL-2 coding sequence resulted in effector cells with nearly as great a cytotoxic effect as resulted from the hIL-2 containing formulation, though the response was not consistent. This effect was not observed in the splenocyte groups, suggesting that the hIL-2 was needed for systemic immunity.

Taken together, the results indicate that treatment with hIL-2 formulations led to both local and systemic anti-tumor immunity, and suggests that this cellular immune response has an effect in slowing tumor growth.

F. Synergistic Effects of IL-2 plasmid and Non-DNA Formulation Components and Effect of hIL-2 Formulation Administration on Production of Secondary Cytokines The effects of the expression of the hIL-2 plasmids in tumor cells on the progress of the mouse tumors demonstrates that such IL-2 expression is effective against such tumors. However, it was also shown that certain immune system effects are also mediated by the lipid components of formulations and that these effects can act synergistically with the IL-2 expression to exercise the antitumor effect.

Intraperitoneal injection of formulated IL-2 plasmid or control DNA elicited the production of IL-12 from peritoneal wash cells. However, production of IFN-γ from those cells was significantly higher when the IL-2 plasmid formulations were injected than when control DNA plasmid formulations were injected. This suggests that the anti-tumor activity of IL-2 expression can be enhanced by formulations which elicit production of $T_H1$ cytokines which act synergistically with the IL-2 expressed from the plasmids.

These results were also suggested by the comparative efficacies of IL-2 formulations containing DOTMA:Chol as compared to formulations containing PVP. While formulations containing PVP resulted in significantly higher expression levels, the DOTMA:Chol formulations had significantly higher antitumor efficacy. Indeed, the efficacy is not directly related to either the total amount of IL-2 encoding DNA injected or to the total amount of lipid used in the formulation.

The production of secondary cytokines following injection of hIL-2 formulations in mice has been studied using RT-PCR for RNA detection and ELISA for protein measurements in tumors and other tissues. For the pro-inflammatory component of the anti-tumor response, the relevant cytokines include tumor necrosis factor-α, IL-1, interferon-γ (IFN-γ), and macrophage chemotactic protein-1 (MCP-1). For generating antigen-specific anti-tumor immune response, IL-12 is required because it promotes a predominantly $T_H1$, or cell-mediated immune response.

Studies were performed on tumor cells (using tumor explants), splenocytes (in vitro and in vivo), and normal bone marrow.

For the in vitro studies, normal splenocytes (triplicate samples of 3×10⁶ cells) were incubated for 24 hr. with the exemplary hIL-2 plasmid formulation or controls (ConA and non-IL-2 formulation). Total RNA was isolated (200 ng), and subjected to reverse transcription using specific primers. The reverse transcription products were then amplified by the PCR for 45 cycles.

The results for the splenocyte in vitro analyses indicate that treatment with either control formulation (without hIL-2 coding sequence) and a formulation containing hIL-2 containing plasmid) both elicited production of murine IFN-γ, and murine MCP-1, but not of murine IL-2 or murine TNF-α.

In vivo analysis of murine cytokine expression by splenocytes was also determined by determining the amount of protein. Following in vivo administration, tumors were explanted and cultured in vitro. Supernatants were tested for cytokine production by ELISA. The results demonstrate that treatment with hIL-2 plasmid formulation results in production of murine IFN-γ and murine IL-12 (approximately 140 and 170 pg/ml respectively). This production was higher than that resulting from treatment with non-hIL-2 control formulation.

G. Biodistribution of IL-2 from Plasmid

Distribution of the hIL-2 plasmid, mRNA transcribed from hIL-2 plasmids, and hIL-2 protein produced from the plasmids can be traced within the body of an organism to which the plasmids have been administered. The tracing can, for example, be performed using approaches such as RT-PCR to detect mRNA and immunohistochemistry to detect hIL-2 protein.

Using RT-PCR, hIL-2 mRNA has been identified in the spleens and draining lymph nodes of treated mice.

H. Toxicity Evaluation of Exemplary Formulations

Figure 9:
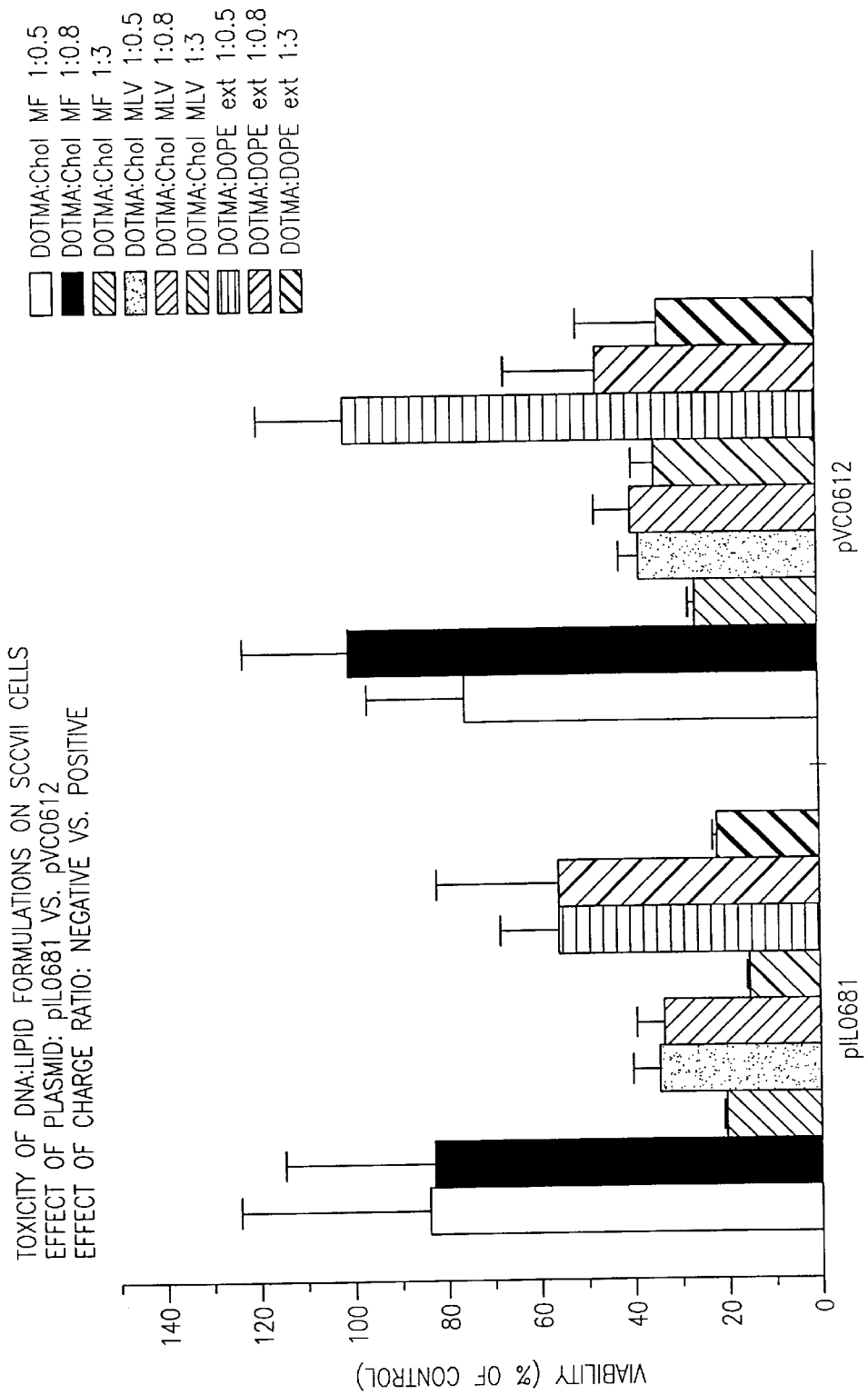
FIG. 9 is a bar graph showing the toxicity effects of lipid formulations having varying charge ratios and methods of liposome formulation.
Figure 10A:
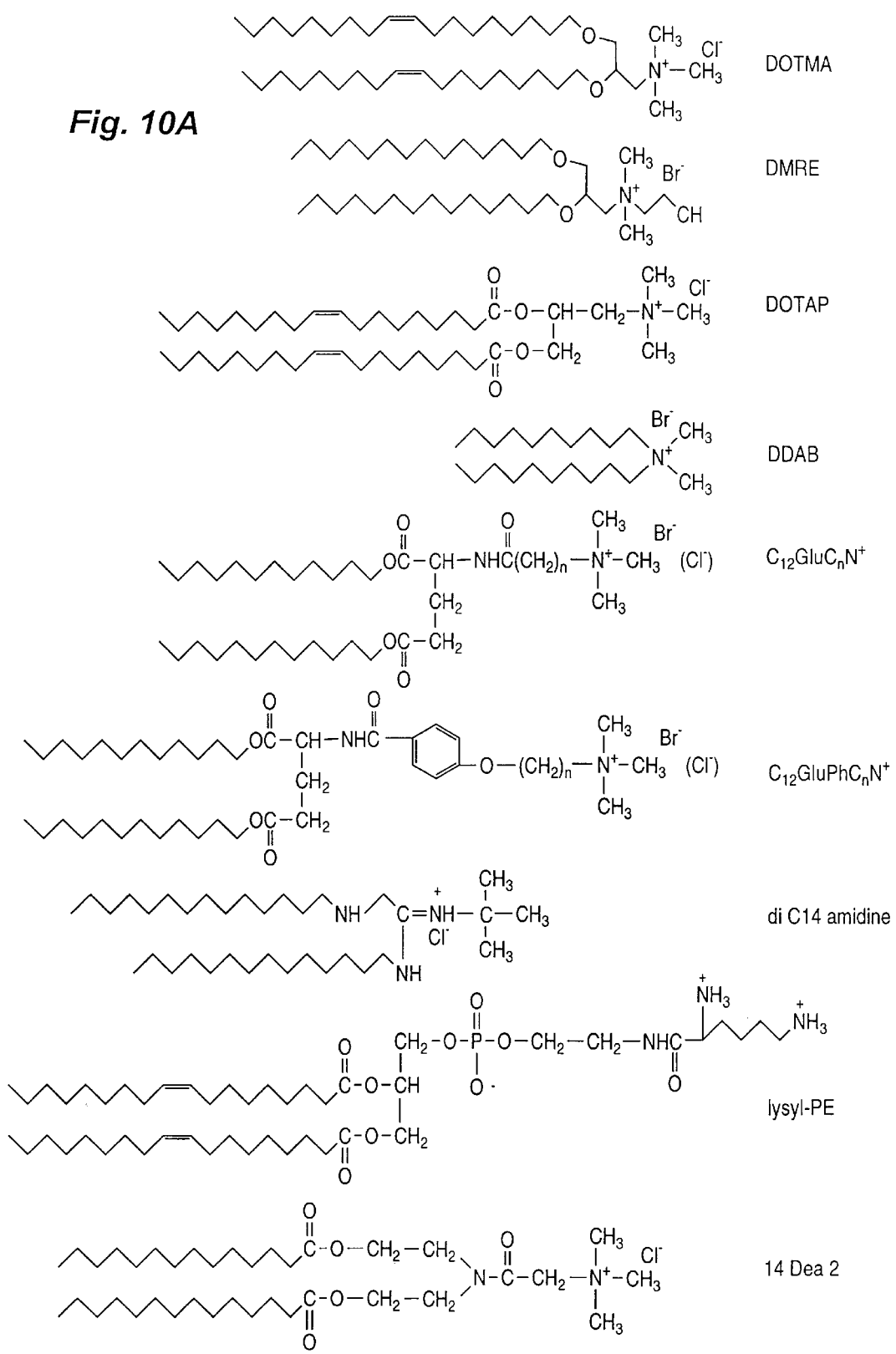
FIG. 10 shows the structures of a number of lipids which have been suggested for use in gene delivery and gene therapy.
Figure 10B:
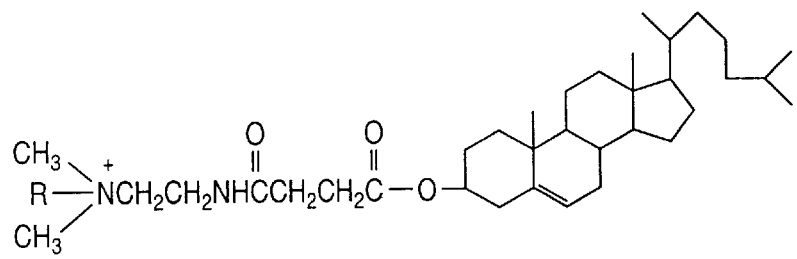
Figure 10B:
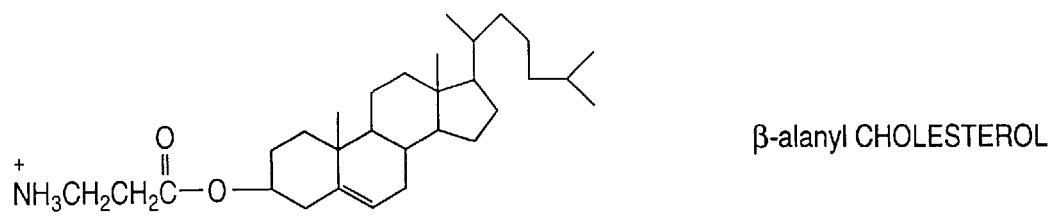
Figure 10B:
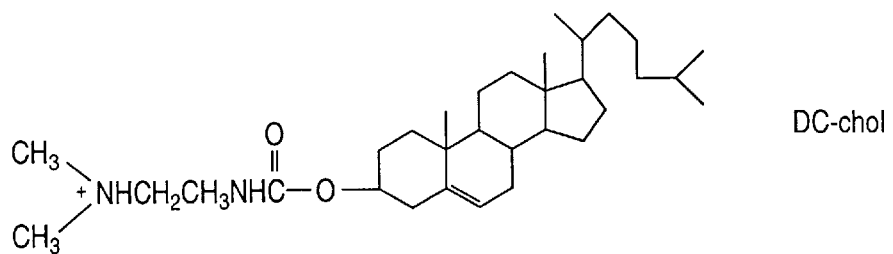
Figure 10C:
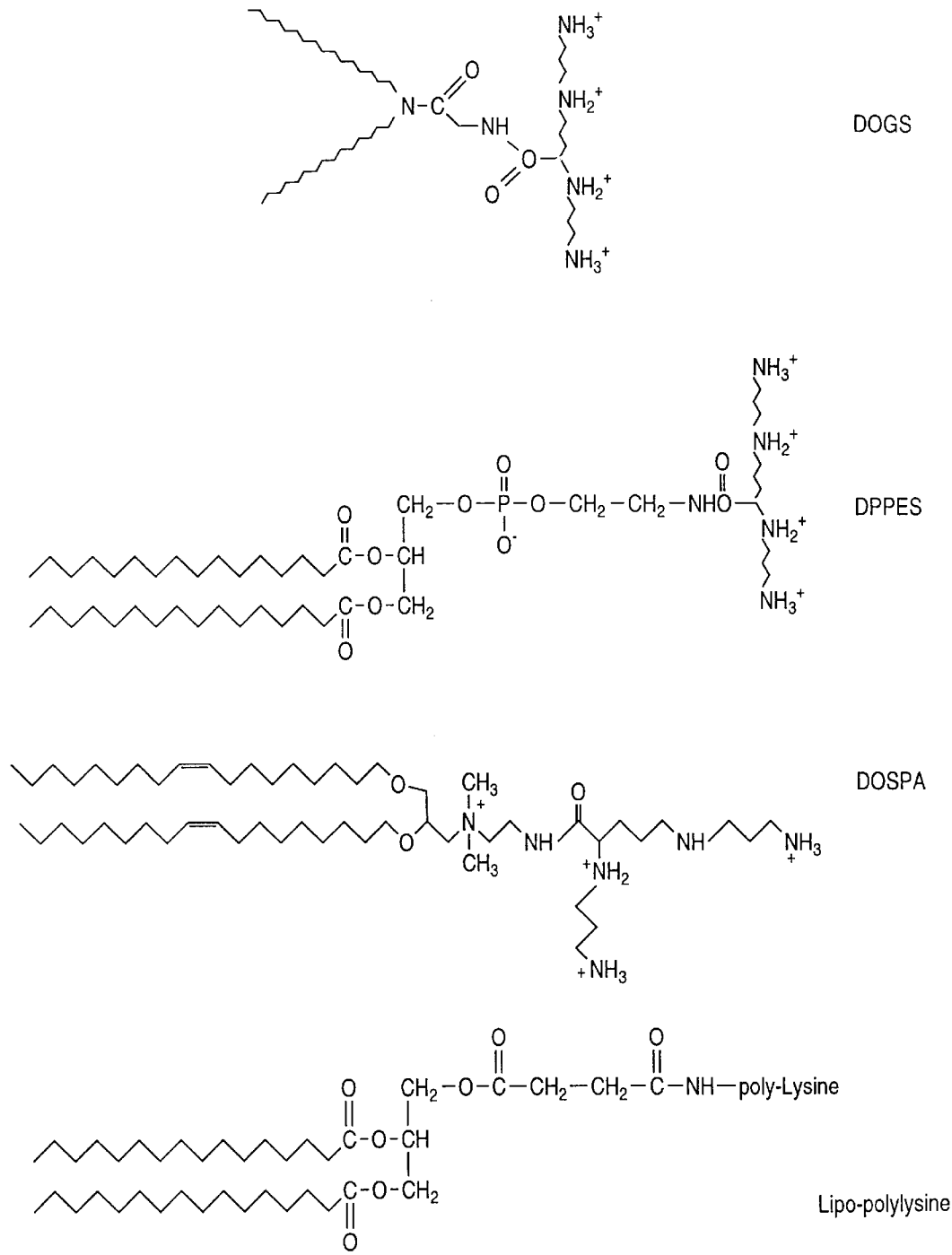
Figure 10D:
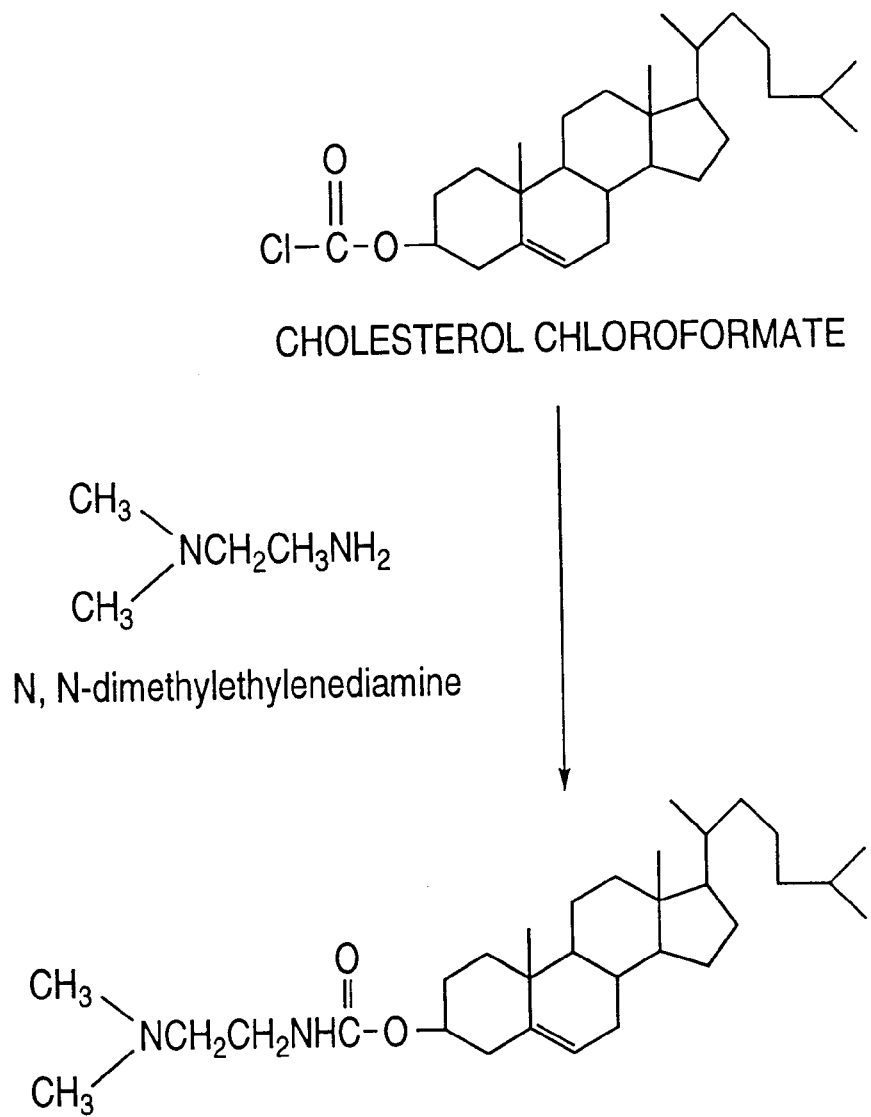

The toxicity of various formulations containing DOTMA with a neutral colipid (either Chol or DOPE) in which the negative to positive charge ratio ranged from 1:3 to 1:0.5. The effects of the formulation was tested against SCC VII cells in RPMI 1640 with 12.5% FBS. 5 μl of formulation solution was added to approximately 0.5 ml of medium and incubated for 48 hrs. As shown in FIG. 9, the formulations having a 1:0.5 and 1:0.8 charge ratio had higher rates of viable cells at the end of the 48 hr test period than those with 1:3 charge ratios. Formulations prepared from liposome prepared by microfluidization generally resulted in higher cell viability rates than those prepared by extrusion or standard solvent evaporation/rehydration methods. Thus, the exemplary formulations do not show high cellular toxicity at the concentrations tested, suggesting that the formulations do not significantly kill cells by direct toxic action in vivo.

V. Administration

Administration as used herein refers to the route of introduction of a plasmid or carrier of DNA into the body. In addition to the methods of delivery described above, the expression systems constructs and the delivery system formulations can be administered by a variety of different methods.

Administration can be directly to a target tissue or by targeted delivery to the target tissue after systemic administration. In particular, the present invention can be used for treating disease by administration of the expression system or formulation to the body in order to establishing controlled expression of any specific nucleic acid sequence within tissues at certain levels that are useful for gene therapy.

The preferred means for administration of vector and use of formulations for delivery are described above. The preferred embodiments are by direct injection using needle injection.

The route of administration of any selected vector construct will depend on the particular use for the expression vectors. In general, a specific formulation for each vector construct used will focus on vector uptake with regard to the particular targeted tissue, followed by demonstration of efficacy. Uptake studies will include uptake assays to evaluate cellular uptake of the vectors and expression of the DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

Muscle cells have the unique ability to take up DNA from the extracellular space after simple injection of DNA particles as a solution, suspension, or colloid into the muscle. Expression of DNA by this method can be sustained for several months.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. Preferably, the complex includes DNA, a cationic lipid, and a neutral lipid in particular proportions. The characteristics of the complex formed with the vector (size, charge, surface characteristics, composition) determines the bioavailability of the vector within the body. Other elements of the formulation function as ligand which interact with specific receptors on the surface or interior of the cell. Other elements of the formulation function to enhance entry into the cell, release from the endosome, and entry into the nucleus.

Delivery can also be through use of DNA transporters. DNA transporters refers to molecules which bind to DNA vectors and are capable of being taken up by epidermal cells. DNA transporters contain a molecular complex capable of noncovalently binding to DNA and efficiently transporting the DNA through the cell membrane. It is preferable that the transporter also transport the DNA through the nuclear membrane. See, e.g., the following applications all of which (including drawings) are hereby incorporated by reference herein: (1) Woo et al., U.S. Ser. No. 07/855,389, entitled "A DNA Transporter System and Method of Use", filed Mar. 20, 1992, now abandoned; (2) Woo et al., PCT/US93/02725, International Publ. WO93/18759, entitled "A DNA Transporter System and method of Use", (designating the U.S. and other countries) filed Mar. 19, 1993; (3) continuation-in-part application by Woo et al., entitled "Nucleic Acid Transporter Systems and Methods of Use", filed Dec. 14, 1993, U.S. Ser. No. 08/167,641; (4) Szoka et al. U.S. Ser. No. 07/913,669, entitled "Self-Assembling Polynucleotide Delivery System", filed Jul. 14, 1992 and (5) Szoka et al., PCT/US93/03406, International Publ. WO93/19768 entitled "Self-Assembling Polynucleotide Delivery System", (designating the U.S. and other countries) filed Apr. 5, 1993. A DNA transporter system can consist of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine. One element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Szoka patent cited above.

Transfer of genes directly into a tumor has been very effective. Experiments show that administration by direct injection of DNA into tumor cells results in expression of the gene in the area of injection. Injection of plasmids containing hIL-2 results in expression of the gene for at least two days at relatively constant levels. The injected DNA appears to persist in an unintegrated extrachromosomal state. This means of transfer is a preferred embodiment.

Administration may also involve lipids as described in preferred embodiments above. The lipids may form liposomes which are hollow spherical vesicles composed of lipids arranged in unilamellar, bilamellar, or multi-lamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblast genetically engineered to express recombinant human growth hormone can secrete the growth hormone into the animal's blood. Secretion of the incorporated gene can be sustained over periods up to 3 months.

Myoblasts eventually differentiate and fuse to existing muscle tissue. Because the cell is incorporated into an existing structure, it is not just tolerated but nurtured. Myoblasts can easily be obtained by taking muscle tissue from an individual who needs gene therapy and the genetically engineered cells can also be easily put back with out causing damage to the patient Is muscle. Similarly, keratinocytes may be used to delivery genes to tissues. Large numbers of keratinocytes can be generated by cultivation of a small biopsy. The cultures can be prepared as stratified sheets and when grafted to humans, generate epidermis which continues to improve in histotypic quality over many years. The keratinocytes are genetically engineered while in culture by transfecting the keratinocytes with the appropriate vector. Although keratinocytes are separated from the circulation by the basement membrane dividing the epidermis from the dermis, human keratinocytes secrete into circulation the protein produced.

The chosen method of delivery should result in expression of the gene product encoded within the nucleic acid cassette at levels which exert an appropriate biological effect. The rate of expression will depend upon the disease, the pharmacokinetics of the vector and gene product, and the route of administration, but should be in the range 0.001–100 mg/kg of body weight /day, and preferably 0.01–10 mg/kg of body weight/day. This level is readily determinable by standard methods. It could be more or less depending on the optimal dosing. The duration of treatment will extend through the course of the disease symptoms, possibly continuously. The number of doses will depend upon the disease, delivery vehicle, and efficacy data from clinical trials.

One skilled in the art will readily appreciate that the present invention is well adapted to obtain the ends and advantages mentioned as well as those inherent therein. The plasmid constructs described herein along with the formulations, methods, procedures, and treatments are presently representative of exemplary preferred embodiments, and are not intended as limitations on the scope of the invention. Changes therein and other uses will occur to those skilled in the art, and are encompassed within the spirit of the invention or defined by the scope of the claims.

It will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, in particular embodiments, the term "comprising" may be replaced by "consisting essentially of".

All patents and publications mentioned in the specification are herein incorporated by reference to the same extent as if each individual publication was specifically and individually indicated to be incorporated by reference.

What we claim is:

1. A plasmid for expression of a human IL-2 coding sequence comprising optimal human codon usage, which comprises: a promoter/enhancer transcriptionally linked to a synthetic human IL-2 coding sequence comprising SEQ. ID NO. 2, and a human growth hormone 3'-untranslated region/poly(a) signal sequence.

2. A composition for expression of a human IL-2 coding sequence comprising optimal human codon usage, which comprises: a cationic lipid; and a plasmid, wherein said plasmid comprises a promoter/enhancer transcriptionally linked to a synthetic human IL-2 coding sequence comprising SEQ. ID NO. 2, and a human growth hormone 3'-untranslated region/poly(a) signal sequence.

3. The composition of claim 2, wherein said cationic lipid is DOTMA, and further comprising
a neutral co-lipid.

4. The composition of claim 3, wherein said neutral co-lipid is cholesterol.

5. The composition of claim 3, wherein said DOTMA and said cholesterol are prepared as liposomes having a diameter of about 100 nm.

6. The composition of claim 5, wherein said cationic lipid and said plasmid are present in amounts such that the negative to positive charge ratio is about (1:0.5).

7. A composition for expression of a human IL-2 coding sequence comprising optimal human codon usage, which comprises: PVP; and a plasmid, wherein said plasmid comprises a promoter/enhancer transcriptionally linked to a synthetic human IL-2 coding sequence comprising SEQ. ID NO. 2, and a human growth hormone 3'-untranslated region/poly(a) signal sequence.

8. A composition for expression of a human IL-2 coding sequence comprising optimal human codon usage, which comprises: DOTMA and cholesterol, prepared as a liposome having a diameter of about 100 nanometers; and a plasmid DNA, wherein said plasmid DNA comprises a transcriptional unit which comprises a synthetic human IL-2 coding sequence comprising SEQ. ID NO. 2 operatively linked to a promoter; and wherein said plasmid and said DOTMA are present in such amounts that the negative to positive charge ratio is about 1:0.5.

9. The composition of claim 8, wherein said plasmid DNA comprises a promoter/enhancer transcriptionally linked to a synthetic human IL-2 coding sequence comprising SEQ. ID NO. 2, and a human growth hormone 3'-untranslated region/poly(a) signal sequence.

10. The composition of claim 8, wherein said plasmid DNA is at least about 80% supercoiled.

11. A method for preparing a composition for expression of a human IL-2 coding sequence comprising optimal human codon usage, comprising the steps of:

(a) preparing a plasmid DNA molecule comprising a transcriptional unit which comprises a synthetic human IL-2 coding sequence comprising SEQ. ID NO. 2 operatively linked to a promoter;

(b) preparing liposomes having a diameter of about 100 nm, wherein said liposomes comprises DOTMA and cholesterol; and (c) combining said liposomes with said DNA in amounts such that said DOTMA and said plasmid DNA are present in amounts such that the negative to positive charge ratio of about 1:0.5.

12. A method for preparing a composition for expression of a human IL-2 coding sequence comprising optimal human codon usage, comprising the steps of:

(a) preparing a plasmid DNA molecule comprising a promoter/enhancer transcriptionally linked to a synthetic human IL-2 coding sequence comprising SEQ. ID NO. 2, and a human growth hormone 3'-untranslated region/poly(a) signal sequence;

(b) preparing liposomes comprising a cationic lipid and a neutral co-lipid; and (c) combining said liposomes with said DNA molecule.

13. The method of claim 12, wherein said cationic lipid is DOTMA and said neutral co-lipid is cholesterol.

14. The method of claim 13, wherein said liposomes have a diameter of about 100 nm.

15. The method of claim 13, wherein said DNA molecule and said cationic lipid are present in such amounts that the negative to positive charge ratio is about (1:0.5).

16. A method for treatment of cancer in a mammal, comprising administering by intratumoral injection to a mammal suffering from cancer a therapeutically effective amount of a composition comprising DOTMA, cholesterol, and a plasmid DNA molecule, wherein said plasmid comprises a promoter/enhancer transcriptionally linked to a synthetic human IL-2 coding sequence comprising SEQ. ID NO. 2, and a human growth hormone 3'-untranslated region/poly(a) signal sequence, wherein said DOTMA and said plasmid DNA are present in amounts such that the negative to positive charge ratio of about 1:0.5, and wherein the expression of said IL-2 sequence results in the inhibition of tumor growth.

17. The method of claim 16, wherein said DOTMA and said cholesterol are prepared as liposomes having a diameter of about 100 nm.

* * * * *